United States Patent
Herold et al.

(10) Patent No.: US 9,611,290 B2
(45) Date of Patent: *Apr. 4, 2017

(54) TRYPSIN-LIKE SERINE PROTEASE INHIBITORS, AND THEIR PREPARATION AND USE

(71) Applicant: THE MEDICINES COMPANY (LEIPZIG) GMBH, Leipzig (DE)

(72) Inventors: Peter Herold, Munchenstein (CH); Mohammed Daghish, Leipzig (DE); Stjepan Jelakovic, Freiburg (DE); Friedrich-Alexander Ludwig, Leipzig (DE); Claudia Reichelt, Leipzig (DE); Alexander Schulze, Bad Liebenwerda (DE); Andrea Schweinitz, Jena (DE)

(73) Assignee: THE MEDICINES COMPANY (LEIPZIG) GMBH, Leipzig (DE)

( * ) Notice: Subject to any disclaimer, the term of this patent is extended or adjusted under 35 U.S.C. 154(b) by 186 days.

This patent is subject to a terminal disclaimer.

(21) Appl. No.: 14/068,657

(22) Filed: Oct. 31, 2013

(65) Prior Publication Data

US 2014/0073573 A1    Mar. 13, 2014

Related U.S. Application Data

(62) Division of application No. 13/015,734, filed on Jan. 28, 2011, now Pat. No. 8,598,206.

(60) Provisional application No. 61/299,054, filed on Jan. 28, 2010.

(51) Int. Cl.
| | | |
|---|---|---|
| *A61K 31/445* | (2006.01) | |
| *C07K 5/078* | (2006.01) | |
| *C07D 211/34* | (2006.01) | |
| *C07D 401/12* | (2006.01) | |
| *C07D 413/12* | (2006.01) | |
| *C07K 5/065* | (2006.01) | |
| *A61K 38/00* | (2006.01) | |

(52) U.S. Cl.
CPC ........ *C07K 5/06139* (2013.01); *C07D 211/34* (2013.01); *C07D 401/12* (2013.01); *C07D 413/12* (2013.01); *C07K 5/06078* (2013.01); *A61K 31/445* (2013.01); *A61K 38/00* (2013.01)

(58) Field of Classification Search
CPC .......................... A61K 31/445; A61K 31/155
See application file for complete search history.

(56) References Cited

U.S. PATENT DOCUMENTS

| | | |
|---|---|---|
| 2005/0119190 A1 | 6/2005 | Sturzebecher et al. |
| 2006/0148901 A1 | 7/2006 | Sturzebecher et al. |
| 2007/0066539 A1 | 3/2007 | Sturzebecher et al. |

FOREIGN PATENT DOCUMENTS

WO    2008-049595    5/2008

OTHER PUBLICATIONS

International Search Report for PCT/US2011/022863, dated Oct. 18, 2011.

*Primary Examiner* — Samira Jean-Louis
(74) *Attorney, Agent, or Firm* — Wenderoth, Lind & Ponack, L.L.P.

(57) ABSTRACT

The invention provides compounds that are effective as inhibitors of human plasmin and plasma kallikrein, and that are useful for the prevention of blood loss and as components of fibrin adhesives. The invention further provides methods of making and using the compounds.

7 Claims, No Drawings

TRYPSIN-LIKE SERINE PROTEASE INHIBITORS, AND THEIR PREPARATION AND USE

FIELD OF THE INVENTION

The invention relates to the fields of organic chemistry, serine proteases (particularly plasmin and plasma kallikrein), and hemostasis, and to therapeutic modulation of the blood coagulation cascade and fibrinolysis.

BACKGROUND OF THE INVENTION

Plasmin (EC 3.4.21.7, fibrinolysin) is a trypsin-like serine protease which effects protein cleavage at arginine or lysine residues; its principal substrates are fibrin and extracellular matrix (ECM) proteins like fibronectin. Other plasmin substrates include various proteins of the basal membrane, for example, laminin and type IV collagen, and zymogens such as the proforms of urokinase and matrix metalloproteases. In blood, plasmin is responsible in particular for fibrinolysis, as it cleaves fibrin into soluble fragments. Plasmin is activated by cleavage from its precursor zymogen, plasminogen, by the action of plasminogen activators, principally serine proteases such as urokinase, tPA, and plasma kallikrein (EC 3.4.21.34; kininogenin, PK).

Endogenous plasmin inhibitors such as $\alpha_2$-macroglobulin and $\alpha_2$-antiplasmin, by moderating the anticoagulant effects of plasminogen activators, play key roles in regulating fibrinolysis. Certain pathological conditions (hyperplasminemias) are characterized by dysregulation of plasmin and spontaneous activation of fibrinolysis. The resulting degradation of wound-closing fibrin is exacerbated by the anticoagulant properties of the fibrinogen degradation products, leading to a serious impairment of hemostasis.

Antifibrinolytic drugs are used clinically to treat such conditions; among the commonly used agents are synthetic amino-substituted carboxylic acids such as p-aminomethylbenzoic acid, ε-aminocaproic acid, and trans-4-(aminomethyl)-cyclohexanecarboxylic acid (tranexamic acid). These compounds block the binding of plasminogen to fibrin, and thus inhibit the generation of plasmin, but they are not direct inhibitors of plasmin and do not inhibit the activity of already-formed plasmin. A direct antifibrinolytic is aprotinin (TRASYLOL™, Bayer AG, Leverkusen), a 58 amino acid polypeptide obtained from bovine lung. Aprotinin inhibits plasmin with an inhibition constant of 1 nM, but is relatively nonspecific: it effectively inhibits trypsin ($K_i$=0.1 nM), plasma kallikrein ($K_i$=30 nM) and, to a lesser extent, a variety of other enzymes.

The principal use of aprotinin was for reduction of blood loss, especially in cardiac surgical procedures with cardiopulmonary bypass (CPB), where it distinctly reduced the need for perioperative blood transfusions (Sodha et al., Expert Rev. Cardiovasc. Ther., 4, 151-160, 2006). Aprotinin was also employed to inhibit blood loss in other operations, for example in organ transplants; it is also used in conjunction with fibrin adhesives.

The use of aprotinin has several disadvantages. Since it is isolated from bovine organs, there is in principle the risk of pathogenic contamination and allergic reactions. The risk of anaphylactic shock is relatively low with the first administration of aprotinin (<0.1%), but increases on repeated administration within 200 days to 4-5%. It has been reported that administration of aprotinin, in direct comparison with ε-aminocaproic acid or tranexamic acid, induces an increased number of side effects (Mangano et al., New Engl. J. Med., 354, 353-365, 2006). Administration of aprotinin led to a doubling of the number of cases of kidney damage requiring dialysis, and the incidence of myocardial infarction and apoplectic stroke was increased in comparison with the control groups. After the Blood Conservation Using Antifibrinolytics in a Randomized Trial (BART) study had shown an increased risk of mortality associated with aprotinin use compared to lysine analogues in high-risk cardiac surgery patients (Fergusson et al., New Engl. J. Med., 358, 2319-2331, 2008), the drug was withdrawn from the market.

A number of synthetic inhibitors of plasmin have been disclosed. Sanders (Sanders and Seto, J. Med. Chem., 42, 2969-2976, 1999) has described 4-hetero cyclohexanone derivatives with relatively weak activity, with inhibition constants of ≥50 µM for plasmin Xue (Xue and Seto, J. Med. Chem., 48, 6908-6917, 2005) has reported on peptidic cyclohexanone derivatives with $IC_{50}$ values ≥2 µM, but no further development has been reported. Okada (Okada et al., Chem. Pharm. Bull., 48, 1964-1972, 2000; Okada et al., Bioorg. Med. Chem. Lett., 10, 2217-2221, 2000) and Tsuda (Tsuda et al., Chem. Pharm. Bull., 49, 1457-1463, 2001) described derivatives of 4-aminomethyl-cyclohexanoic acid which inhibit plasmin with $IC_{50}$ values ≥0.1 µM, but clinical use of these inhibitors has not been reported.

Stürzebecher et al. have described a series of N-terminal sulfonylated benzamidine peptidomimetics having various effects on serine proteases. Included within this class are factor Xa inhibitors, useful as anticoagulants and antithrombotics (U.S. Pat. No. 6,841,701); urokinase inhibitors, useful as tumor suppressors (US Pat. Application Publication No. 2005/0176993, U.S. Pat. No. 6,624,169); inhibitors of plasma kallikrein (PK), factor XIa and factor XIIa, useful as anticoagulants and antithrombotics (US Pat. Application Publication No. 2006/0148901); and matriptase inhibitors, useful as tumor suppressors (US Pat. Application Publication No. 2007/0055065).

Inhibition constants for some compounds affecting plasmin activity have been published in several studies on inhibitors of coagulation proteases. The compounds in question, however, were being investigated as antithrombotics, and therefore a low level of plasmin inhibition was preferred. For example, the thrombin inhibitor melagatran inhibits plasmin with a $K_i$ value of 0.7 µM, and the structurally related compound H317/86 has an inhibition constant of 0.22 µM (Gustafsson et al., Thromb. Haem., 79, 110-118, 1998). However, because both compounds inhibit the protease thrombin much more strongly ($K_i$≤2 nM), the net effect of administration is inhibition of coagulation. The possibility of using such compounds as pro-coagulants, e.g. for reducing blood loss in cardiac surgical procedures, was not mentioned in any of these papers.

As noted above, aprotinin inhibits not only plasmin but also plasma kallikrein (PK). PK is a multifunctional, trypsin-like serine protease for which several physiological substrates are known. Thus, by proteolytic cleavage, PK is able to release the vasoactive peptide bradykinin from high molecular weight kininogen, and to activate zymogens such as coagulation factor XII, pro-urokinase, plasminogen and pro-MMP 3. It is therefore assumed that the PK/kinin system plays an important role in many pathological conditions, for example in thromboembolic situations, disseminated intravascular coagulation, septic shock, allergies, the postgastrectomy syndrome, arthritis and ARDS (adult respiratory distress syndrome) (Tada et al., Biol. Pharm. Bull, 24, 520-524, 2001).

Accordingly, aprotinin, via its inhibitory effect on PK, inhibits the release of the peptide hormone bradykinin, which in turn has various effects via activation of the bradykinin B2 receptor. The bradykinin-induced release of tPA, NO and prostacyclin from endothelial cells (Schmaier, *J. Clin. Invest.*, 109, 1007-1009, 2002) influences fibrinolysis, blood pressure and inflammatory events. It has been suggested that systemic inflammatory processes which may occur as a side effect in surgical operations can be reduced by inhibiting bradykinin release.

Various bisbenzamidines, such as pentamidine and related compounds, and esters of ω-amino- and ω-guanidinoalkyl-carboxylic acids, have been described as PK inhibitors with micromolar $K_i$ values (Asghar et al., *Biochim Biophys Acta*, 438, 250-264, 1976; Muramatu and Fuji, *Biochim. Biophys. Acta*, 242, 203-208, 1971; Muramatu and Fuji, *Biochim. Biophys. Acta*, 268, 221-224, 1972; Ohno et al., *Thromb. Res.*, 19, 579-588, 1980; Muramatu et al., *Hoppe-Seyler's Z. Physiol. Chem.*, 363, 203-211, 1982; Satoh et al., *Chem. Pharm. Bull.*, 33, 647-654, 1985; Teno et al., *Chem. Pharm. Bull.*, 39, 2930-2936, 1991).

The first selective competitive PK inhibitors to be reported (Okamoto et al., *Thromb. Res., Suppl.* VIII, 131-141, 1988) were derived from arginine or phenylalanine, and inhibit PK with $K_i$ values around 1 µM. Several papers on the development of competitive PK inhibitors have been published by the Okada group, with the most active compounds, derived from trans-4-aminomethylcyclohexanecarbonyl-Phe-4-carboxymethylanilide, having inhibition constants around 0.5 µM (Okada et al., Biopolymers, 51, 41-50, 1999; Okada et al., 2000, Tsuda et al., 2001). It is characteristic of these PK inhibitors that they have a relatively high $K_i$ value.

Aliagas-Martin et al., in U.S. Pat. No. 6,472,393, described a wide variety of 4-amidinoanilides which are potent PK inhibitors, having inhibition constants around 1 nM. Antonsson et al. likewise described a wide range of amidine and guanidine PK inhibitors in U.S. Pat. No. 5,602,253. Stürzebecher et al. have described 4-amidino- and 4-guanidino-benzylamines as PK inhibitors, some of which are Factor Xa inhibitors (US Pat. Application Publication. No. 2005/0119190), some of which have a slight inhibitory effect on plasmin (US Pat. Application Publication. No. 2006/0148901), and some of which are dual plasmin/PK inhibitors (PCT Publication No. 2008/049595). These inhibitors are related to, but differ structurally from, the inhibitors described in the present application.

Dyax Corp. has developed a selective plasma kallikrein inhibitor, DX-88 (ecallantide, Kalbitor™), for the treatment of acute attacks in hereditary angioedema. Ecallantide is a recombinant small protein that has been identified utilizing a phage display technology based on the first Kunitz domain of human tissue factor pathway inhibitor (TFPI). Ecallantide is also undergoing phase II clinical testing for the reduction of blood loss during on-pump cardiothoracic surgery (Lehmann, *Expert Opin. Biol. Ther.*, 8, 1187-1199, 2008).

There remains a need for low-molecular-weight substances, suitable for therapeutic applications, which reversibly and competitively inhibit plasmin and plasma kallikrein with high activity and specificity, and the present invention provides such compounds. The compounds of the present invention, accordingly, are suitable for modulating and/or maintaining hemostasis in various situations, particularly during and after surgeries with cardiopulmonary bypass, organ transplants, and other major surgical interventions. It is expected that the compounds of the present invention, as inhibitors of plasma kallikrein, will also lower kinin release, thereby suppressing both kinin-mediated inflammatory reactions and kinin-induced release of tPA from endothelial cells. The latter effect provides an additional mechanism for downregulation of fibrinolysis.

BRIEF DESCRIPTION OF THE INVENTION

It has been found that compounds of general formula I,

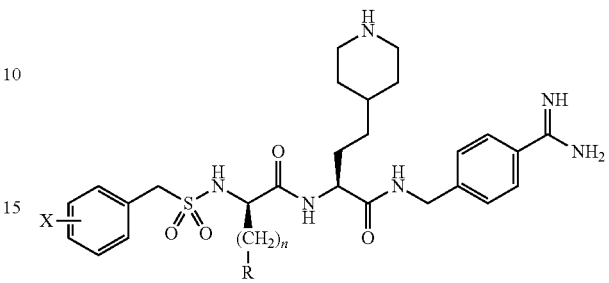

(I)

wherein X, R, and n are as defined below, are effective and selective inhibitors of plasmin and plasma kallikrein. The invention accordingly provides compounds of formula I, methods for the preparation of compounds of formula I, and pharmaceutical compositions comprising compounds of formula I. The invention also provides methods of inhibiting plasmin and/or PK in a patient, methods for therapeutic modulation of the blood coagulation cascade and fibrinolysis, especially methods for prevention and treatment of blood loss in a patient, by administration of the compounds of formula I.

The invention further provides methods for the use of these compounds in manufacturing medicaments for inhibiting plamin and/or PK in a patient, medicaments for therapeutic modulation of the coagulation cascade and fibrinolysis, especially for prevention and treatment of blood loss in a patient. Subjects who may be treated with the compositions of the invention include, but are not limited to, patients experiencing hyperfibrinolytic conditions, organ transplants, and cardiac surgical procedures, especially those involving cardiopulmonary bypass.

In the above formula I, X is selected from the group consisting of H, $CO_2H$, and $CO_2R'$; n ranges from 0 to 3; and R is selected from the group consisting of phenyl, pyridyl, tetrazolyl, and piperidinyl; wherein R may be unsubstituted or may be substituted by one or more substituents, as described in detail below.

The present invention also provides fibrin adhesives comprising the compounds of the invention, and methods for the use of the compounds of the invention in the manufacture of a fibrin adhesive.

DETAILED DESCRIPTION OF THE INVENTION

The invention provides compounds having the following formula (I)

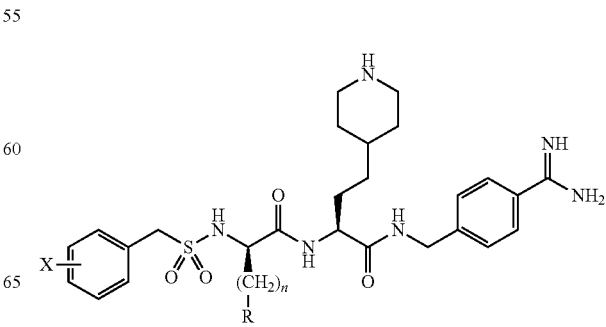

I and pharmaceutically acceptable salts thereof; wherein X is selected from the group consisting of H, CO₂H, and CO₂R'; n ranges from 0 to 3; and R is phenyl, pyridyl, tetrazolyl, or piperidinyl. The moiety R may be unsubstituted or may be substituted by one or more of halogen, R', OR', SR', S=(O)R', S(=O)₂R', S(=O)₂NHR', S(=O)2NR'₂, CN, NH₂, NHR', NR'₂, NHS(=O)₂R', NHC(=O)R', NHC(=O)OR', NHC(=O)NHR', NHC(=O)NR'₂, C(=O)R', C(=O)CH₂OR', CO₂R', C(=O)NHR', or C(=O)NR'₂; and where R is pyridyl, it may be a pyridine N-oxide. In all of the above-described compounds, each R' is independently C₁ to C₄ branched or unbranched lower alkyl or CF₃. As used herein the terms "phenyl", "pyridyl", tetrazolyl, and "piperidinyl" refer to both the unsubstituted and substituted systems, unless specifically identified as being unsubstituted.

In preferred embodiments, n is 2 or 3. R is preferably phenyl, 4-pyridyl, or 4-piperidinyl. Particularly preferred are compounds wherein R is unsubstituted phenyl, unsubstituted 4-pyridyl, unsubstituted 4-pyridyl N-oxide, 1-acetyl-4-piperidinyl, 1-tetrazolyl, 1-isopropionyl-4-piperidinyl, or 1-cyclopropanecarbonyl-4-piperidinyl.

In another preferred embodiment, n is 0 and R is unsubstituted phenyl. In other embodiments, n is 2 or 3, R is 4-piperidinyl; and the nitrogen of the piperidinyl bears a substituent selected from the group consisting of C(=O)R', C(=O)CH₂OR', CO₂R', C(=O)NHR', and C(=O)NR'₂.

Representative examples of the compounds of the invention are set out in Table 1.

TABLE 1

| Compound No. | X | n | R |
|---|---|---|---|
| 1.1 | H | 3 | 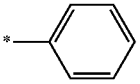 [SMILES: *c1ccccc1] |
| 1.2 | H | 3 | 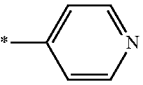 [SMILES: *c1ccncc1] |
| 1.3 | 3-CO₂H | 3 | 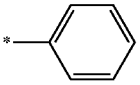 [SMILES: *c1ccccc1] |
| 1.4 | 3-CO₂Me | 3 | 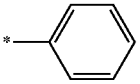 [SMILES: *c1ccccc1] |
| 1.5 | H | 3 | 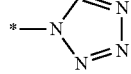 |
| 1.6 | H | 0 | 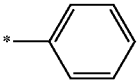 [SMILES: *c1ccccc1] |
| 1.7 | H | 2 | 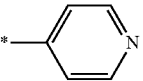 |
| 1.8 | H | 3 |  |

TABLE 1-continued

| Compound No. | X | n | R |
|---|---|---|---|
| 1.9 | H | 2 | 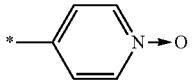 [SMILES: *c1cc[n+]([O-])cc1] |
| 2.1 | H | 2 | 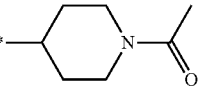 |
| 2.2 | H | 2 | 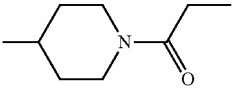 |
| 2.3 | H | 2 | 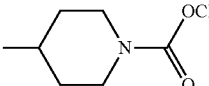 |
| 2.4 | H | 2 | 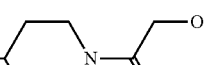 |
| 2.5 | H | 2 |  |
| 2.6 | H | 2 | 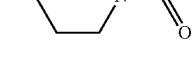 |
| 2.7 | H | 3 | 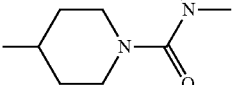 |
| 2.8 | H | 3 | 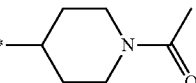 |
| 2.9 | H | 2 | 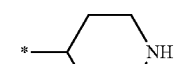 |
| 2.10 | H | 2 | 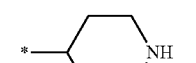 |
| 2.11 | H | 2 |  |
| 2.12 | H | 2 | 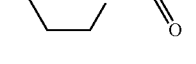 |

TABLE 1-continued

| Compound No. | X | n | R |
|---|---|---|---|
| 2.13 | H | 3 | *-piperidine-N-C(=O)-CH2CH3 |
| 2.14 | H | 3 | *-piperidine-N-C(=O)-cyclopropyl |

The pharmaceutically acceptable salts of the compounds of the invention are preferably formed by addition of any acid known to be useful in the formation of pharmaceutical salts. Preferred acids for salt formation include HCl, HBr, sulfuric acid, phosphoric acid, acetic acid, citric acid, methanesulfonic acid, trifluoroacetic acid, and p-toluenesulfonic acid.

Substituents on the aromatic or heteroaromatic rings R include, but are not limited to, one or more of F, Cl, Br, I, $CF_3$, R', phenyl, OH, OR', $OCF_3$, $CO_2H$, $CO_2R'$, CONHR', $CONR'_2$, $NH_2$, NHR', $NR'_2$, $NHSO_2'$, $NR'SO_2R'$, $NO_2$, SOR', $SO_2R'$, $SO_2NH2$, $SO_2NHR'$, $SO_2NR'_2$, CN, $OCO_2R'$, OCONHR', $OCONR'_2$, NHCOR', $NHCO_2R'$, NHCONHR', $NHCONR'_2$, $NHCO_2R'$, $NR'CO_2R'$, NR'CONHR', and $NR'CONR'_2$, where each R' is independently $C_1$ to $C_4$ branched or unbranched lower alkyl, and cycloalkyl.

The compounds of the general formula I can be prepared by sequential coupling of amino acids to 4-amidinobenzylamine, which is N-protected at the amidino group. It will be understood that any suitable N-protecting group known in the art may be employed at the amidino group. Suitable N-protecting groups for the amidino group include, but are not limited to, 1,2,4-oxadiazol-5-one, N-Boc, N-Cbz, N-benzyloxy, and N-acetoxy. The 1,2,4-oxadiazol-5-one, N-benzyloxy and N-acetoxyamidino groups are preferred, because they are easily prepared from the corresponding nitrile.

The compounds of the invention may be prepared in several ways. Preferred synthetic approaches involve the formation of amide and sulfonamide bonds between pre-synthesized components. The methods and procedures described in PCT Publication No. 2008/049595, which is incorporated herein by reference in its entirety, may be readily adapted to the synthesis of the compounds of the present invention.

As used herein, the expression "an activated carboxylic acid derived from" a given acid refers to derivatives of carboxyxlic acids that are reactive toward amines, including but not limited to active esters, mixed anhydrides, and acyl halides, as are well-known in the art of peptide synthesis. Suitable examples include, but are not limited to, N-hydroxybenzotriazole esters, O-acylated isoureas, pentachloro- and pentafluoro-phenyl esters, acyl chlorides, and mixed anhydrides with carbonic acid monoesters. Preferred activated carboxylic acids are the mixed anhydride obtained by reaction with isobutyl chloroformate, or the N-hydroxybenzotriazole ester.

In a first representative synthesis, an amidino-protected 4-(aminomethyl)-benzamidine, such as 4-(aminomethyl)-N-acetoxybenzamidine (i), is obtained from the commercially available 4-cyanobenzylamine (Showa Denko K.K., Japan) by the method described in the supplement to Schweinitz et al., *J. Biol. Chem.*, 279:33613-33622 (2004). Alternative amidino-protected 4-(methylamino)benzamidines include (ii), (iii), or (iv) as described below. This material is N-acylated with an activated carboxylic acid derived from compound A.

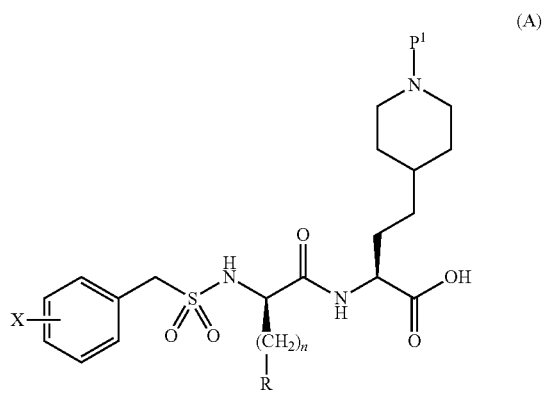

(A)

wherein $P^1$ is an amino protecting group, and X, n, and R are as described above. $P^1$ may be any amino protecting group known in the art, including but not limited to Fmoc, Alloc, Boc, benzyloxycarbonyl (Cbz), 4-nitrobenzyloxycarbonyl (4-$NO_2$-Cbz), trifluoroacetyl, trityl, and benzhydryl. The Boc and the Cbz group are preferred. Following the acylation, cleavage of the amino protecting group $P^1$ and cleavage of the protecting group from the benzamidine are carried out, in any order. If $P^1$ is a benzyloxycarbonyl or benzhydryl group, both protecting groups may be removed in a single hydrogenolysis step. On a small scale, final purification of the inhibitors is preferably carried out by preparative reversed-phase HPLC. Larger preparations are purified by recrystallization of the compound, or a suitably crystalline salt thereof, as is routine in the art.

A second representative synthesis comprises the acylation of 4-(aminomethyl)-N-acetoxybenzamidine (i) (or, alternatively, (ii), (iii), or (iv)) with an activated carboxylic acid derived from compound B,

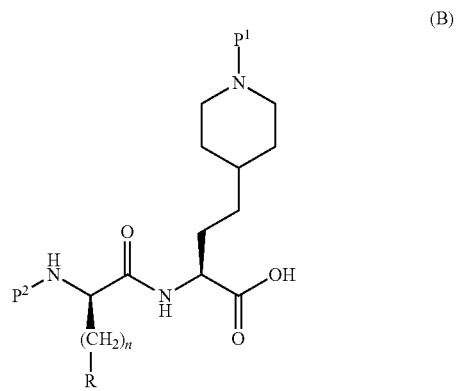

(B)

wherein $P^1$ and $P^2$ are amino protecting groups and n and R are as described above. Again, $P^1$ and $P^2$ may be any amino protecting group known in the art, including but not limited to Fmoc, Alloc, Boc, benzyloxycarbonyl (Cbz), 4-nitrobenzyloxycarbonyl (4-$NO_2$-Cbz), trifluoroacetyl, trityl, and benzhydryl. In this scheme, however, $P^1$ and $P^2$ are preferably orthogonal, so that $P^2$ may be cleaved without affecting $P^1$.

After the acylation, the amino protecting group $P^2$ is cleaved, and the resulting deprotected α-amino group is sulfonylated with a sulfonylating agent of formula C:

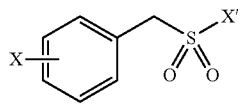
(C)

wherein X' is a leaving group, preferably Cl, and X is as defined above. After sulfonylation, the amino protecting group $P^1$ and the protecting group on the benzamidine are cleaved as described above, simultaneously or in any order.

A third, and preferred, synthetic approach comprises the acylation of 4-(aminomethyl)-N-acetoxybenzamidine (i) (or, alternatively, (ii), (iii), or (iv)) with an activated carboxylic acid derived from compound D

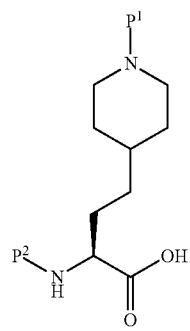
(D)

wherein $P^1$ and $P^2$ are amino protecting groups as described above.

Again, $P^1$ and $P^2$ are preferably orthogonal, so that $P^2$ may be cleaved without affecting $P^1$. After the acylation, the amino protecting group $P^2$ is cleaved, to generate an intermediate such as E shown below:

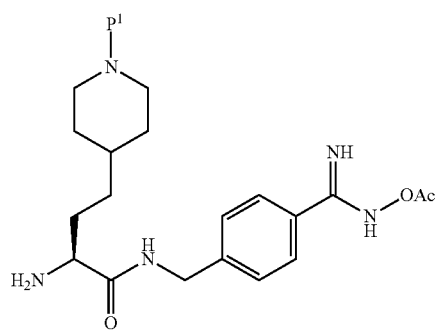
(E)

In this manner, using the starting materials (ii)-(v) described above, the invention also provides compounds analogous to E, such as the following:

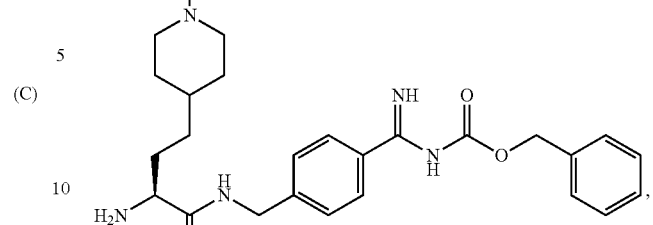

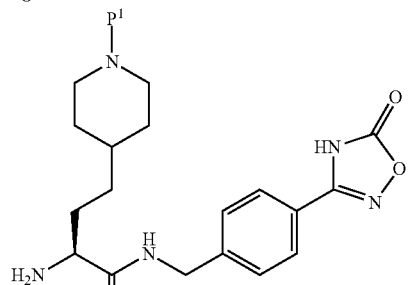

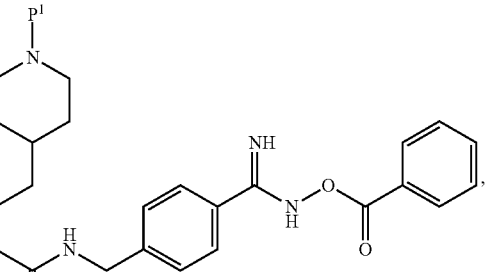

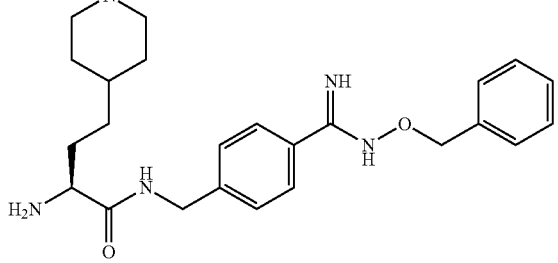

where $P^1$ is an amino protecting group as described above.

The intermediate E is then acylated with an activated carboxylic acid derivative derived from compound F

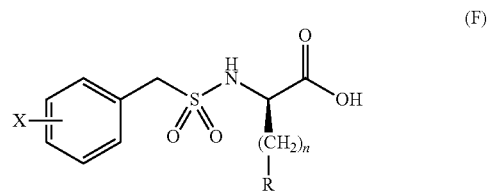
(F)

where X, n, and R are as defined above. Removal of $P^1$ and the amidine protecting group, as described above, provides a compound of structure I.

A fourth method comprises acylation of an N-acylated amidino-protected 4-(aminomethyl)benzamidine, such as structure E

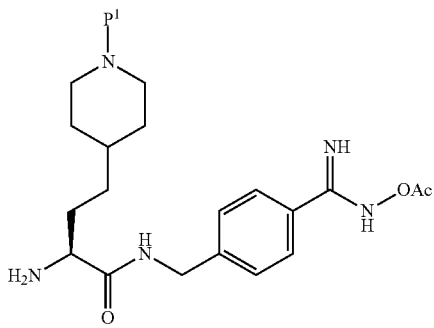

with an activated carboxylic acid derived from structure G

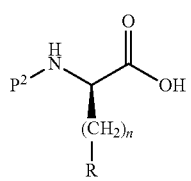

where $P^1$, $P^2$, n and R are as defined above.

The invention provides a variety of compounds of formula G, and precursors thereof, including but not limited to the following examples:

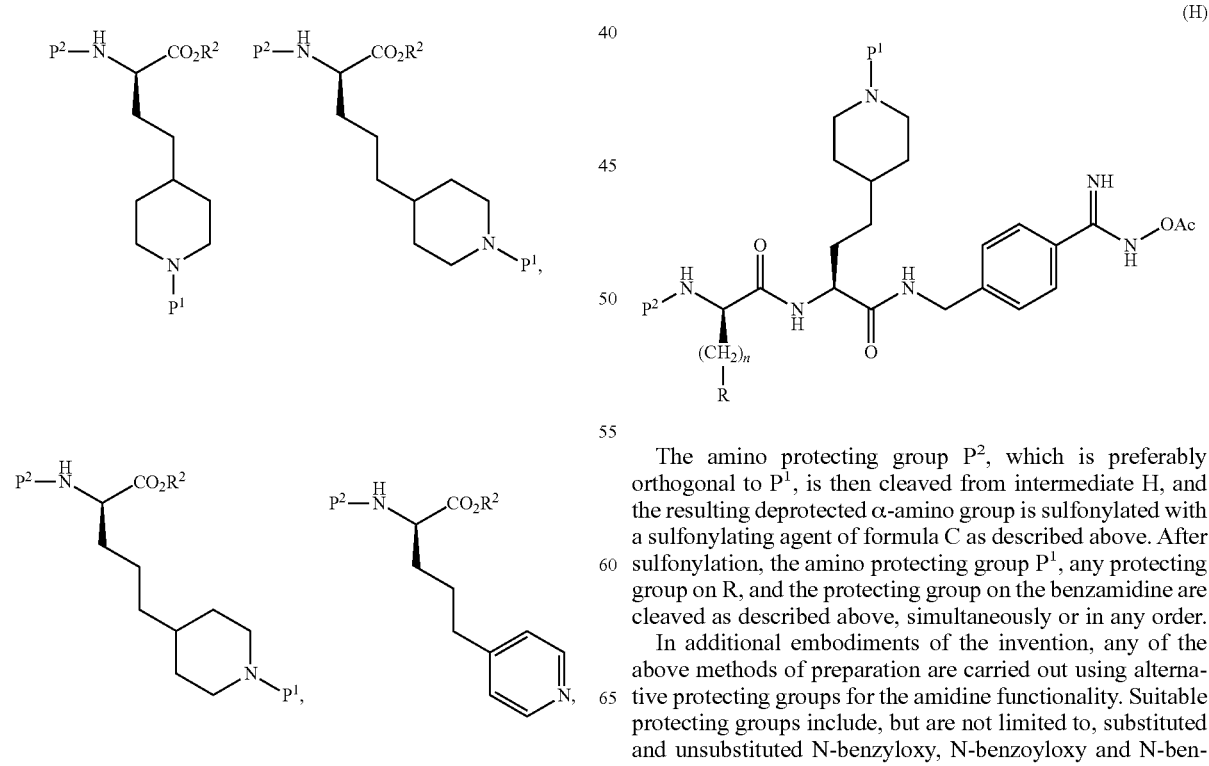

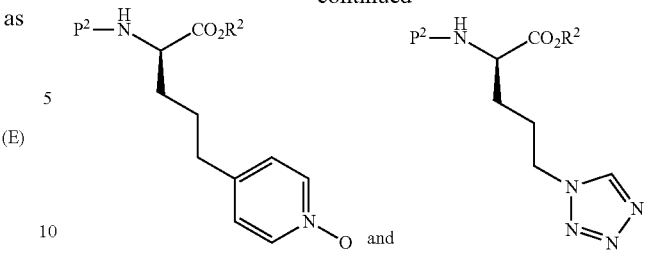

wherein $P^1$ and $P^2$ are independently H or amino protecting groups, such as Boc, Fmoc, Cbz, and trifluoroacetyl, and $R^2$ may be H, methyl, ethyl, t-butyl, or benzyl. Preferably, $P^1$ and $P^2$ are orthogonal, so that $P^2$ can be removed in the presence of $P^1$. Particularly useful as intermediates are compounds of formula

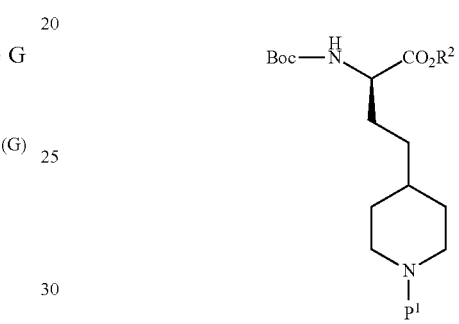

where $P^1$ is H, benzyloxycarbonyl, or 4-nitrobenzyloxycarbonyl, and $R^2$ is H, methyl, ethyl, t-butyl, or benzyl.

Acylation of a compound E with an activated acid derived from structure G yields intermediates such as structure H The amino protecting group $P^2$, which is preferably orthogonal to $P^1$, is then cleaved from intermediate H, and the resulting deprotected α-amino group is sulfonylated with a sulfonylating agent of formula C as described above. After sulfonylation, the amino protecting group $P^1$, any protecting group on R, and the protecting group on the benzamidine are cleaved as described above, simultaneously or in any order.

In additional embodiments of the invention, any of the above methods of preparation are carried out using alternative protecting groups for the amidine functionality. Suitable protecting groups include, but are not limited to, substituted and unsubstituted N-benzyloxy, N-benzoyloxy and N-benzyloxycarbonyl groups, and the 1,2,4-oxadiazol-5-one heterocyclic ring, which are readily introduced by the substitution for (i) of alternative starting materials such as (ii)-(v) shown below:

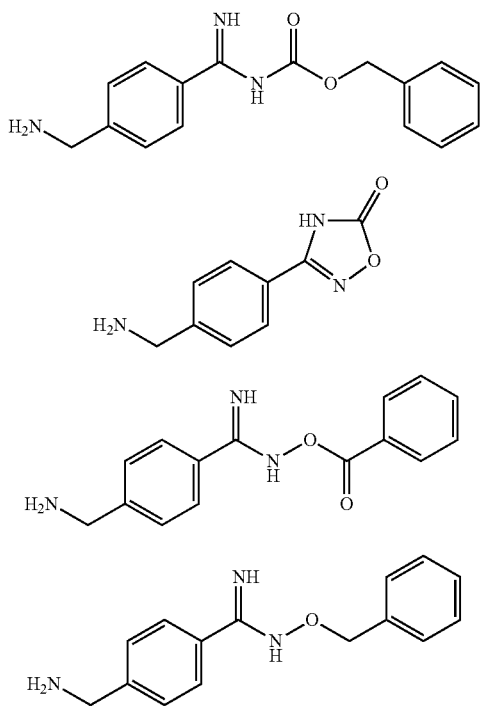

The compounds of the invention are useful for the therapeutic modulation of the blood coagulation cascade and fibrinolysis. As used herein, "therapeutic modulation" includes both pro- and anti-coagulant activities, and the in vivo stabilization or promotion of innate hemostatic or fibrinolytic activities. In particular, the compounds are useful for the prevention or treatment of blood loss. Patients in need of such treatment include those undergoing surgery (especially those procedures, such as cardiac surgery, which involve cardiopulmonary bypass), and those suffering from an acquired or inborn derangement of hemostasis or fibrinolysis.

The invention also provides pharmaceutical composition comprising one or more compounds of the invention, in combination with one or more pharmaceutically acceptable carriers or excipients. Such excipients include, but are not limited to, fillers, binding agents, lubricants, preservatives, water, buffers, and disintegrants. The compositions may be in the form of solids or liquids, compounded for oral administration, or solutions or suspensions suitable for parenteral administration. In particular, a buffered saline solution suitable for parenteral administration is provided, as are powdered or lyophilized compositions suitable for reconstitution into a buffered saline solution.

Also provided are fibrin adhesives comprising, in at least one component of the fibrin adhesive, one or more compounds of formula I. Methods and compositions for fibrin adhesives are well-known in the art; see Sierra, *J. Biomater. Appl.*, 7:309-352 (1993). Fibrin adhesives generally consist of a physiological two-component adhesive which comprises as a first component fibrinogen, factor XIII and aprotinin, and as a second component thrombin and calcium chloride for factor XIII activation. In such compositions, the prior art material aprotinin will be augmented or replaced by a suitable plasmin inhibitor of the present invention. Methods and materials for preparing fibrin adhesives are described in U.S. Pat. No. 7,572,769, which is incorporated by reference in its entirety. Compositions without fibrinogen may also be prepared, as described in U.S. Pat. No. 6,410,260, which is incorporated herein by reference in its entirety.

The invention also provides methods for preventing blood loss in a patient, which comprise administering to a patient in need thereof an effective amount of at least one compound of formula I. Such patients include, but are not limited to, individuals with hyperfibrinolytic conditions, or undergoing organ transplants or cardiac surgical procedures, in particular those procedures involving cardiopulmonary bypass. Preferably the compound or compounds are administered in the form of a pharmaceutical composition as described above. Those skilled in the art will appreciate that suitable doses will vary with the particular compound, the route of administration, the condition to be treated, and the hemomstatic status of the patient. In general, daily doses in the range of 1 mg to 500 mg will be effective. Effective dosing levels can be determined by dose-ranging studies, which are routine and well within the ability of those skilled in the art. Dosing may be continuous (e.g., via an intravenous line), or unit doses can be administered one or more times daily, as needed to maintain an effective concentration in vivo. Preferably, dosing is adjusted so as to maintain a mean blood level ranging from 0.01 to 10 ng/ml during the period for which prevention of blood loss is desired.

The invention further provides methods for inhibiting human plasmin and/or PK, in a patient in need thereof, comprising administering to said patient an effective amount of one or more compounds of formula I. Effective doses are determined as described above.

The invention also provides for the use of a compound of formula I in the manufacture of medicaments for the prevention of blood loss, the inhibition of plasmin, and/or the inhibition of PK, and in the manufacture of a fibrin adhesive.

The following examples are presented by way of example, and are intended to illustrate and explain the invention in detail. The scope of the invention is not limited to the examples presented.

EXAMPLES

Analytical HPLC

| Variable | Parameters |
| --- | --- |
| Device | Shimadzu LC-10A system |
| Column | Phenomenex Luna $C_{18}$ 100 Å, 5 µm column, 4.6 × 250 mm |
| Mobile phase | A: TFA, 0.1% (v/v) in water; B: TFA, 0.1% (v/v) in methanol |
| Method | Linear gradient of 1% B per min |
| Flow rate | 1.0 mL/min |
| Detection wavelength | UV 220 nm |
| Column temperature | 25° C. |
| Injection volume | 30 µl |

Preparative HPLC

| Variable | Parameters |
| --- | --- |
| Device | Shimadzu LC-8A system |
| Column | Phenomenex Luna $C_8(2)$ 100 Å, 5 µm column, 30 × 250 mm |
| Mobile phase | A: TFA, 0.1% (v/v) in $H_2O$; B: TFA, 0.09% (v/v) in methanol |
| Method | Linear gradient of 45% B in 120 min |
| Flow rate | 20.0 mL/min |
| Detection wavelength | UV 220 nm |
| Column temperature | 30° C. |

Chiral HPLC

| Variable | Parameters |
| --- | --- |
| Device | HP Agilent 1100 system |
| Column | Chiralpak AD-H 5 µm column, 4.6 × 250 mm |
| Mobile phase | A: heptane; B: isopropanol |
| Method | isocratic 85% A/15% B 45 min |
| Flow rate | 1.0 mL/min |
| Detection wavelength | UV 220 nm |
| Column temperature | 25° C. |
| Injection volume | 30 µl |

Thin Layer Chromatography

Thin layer chromatography (TLC) of final inhibitors was performed on silica gel plates (silica gel 60 $F_{254}$, Merck, Darmstadt, Germany) using the following mobile phase systems (solvent ratios are by volume):

| | |
| --- | --- |
| n-butanol/acetic acid/water | 4/1/1 |
| n-butanol/acetic acid/ethyl acetate/water | 1/1/1/1 |
| dichloromethane/methanol (DCM/MeOH) | 5/1 |
| benzene/acetone/acetic acid (BAE) | 27/10/05 |
| petrol ether (PE)/ethyl acetate (EE) | 1/1 |

Mass Spectroscopy

Mass spectra were recorded on an Esquire HCT ESI-MS (Bruker Daltonics).

Abbreviations

4-Amba 4-amidinobenzylamide
Ac acetyl
Boc tert.-Butyloxycarbonyl
BSA bovine serum albumin
Bzls benzylsulfonyl
Cbz benzyloxycarbonyl
Cbz(4-$NO_2$) (4-nitro)benzyloxycarbonyl
DCM dichloromethane
DGly(Tzlpr) (R)-2-amino-5-(1H-tetrazol-1-yl)pentanoic acid
DGly(4-Pippr) (R)-2-amino-5-(piperidine-4-yl)pentanoic acid
DGly(4-Pyrpr) (R)-2-amino-5-(pyridine-4-yl)pentanoic acid
DGly(4-Pyrpren) (R,E)-2-amino-5-(pyridine-4-yl)pent-4-enoic acid
DhAla(4-Pip) (R)-2-amino-4-(piperidine-4-yl)butanoic acid
D/LhAla(4-Pyr) (R,S)-2-amino-4-(pyridine-4-yl)butanoic acid
DPhg (R)-2-amino-2-phenylacetic acid
DPpg (R)-2-amino-5-phenylpentanoic acid
DIEA diisopropylethylamine
DMF N,N-dimethylformamide
DMSO dimethyl sulfoxide
FC flash chromatography
HPLC high performance liquid chromatography
m-CPBA 3-chloroperoxybenzoic acid
MS mass spectroscopy
NMM N-Methylmorpholine
PyBop benzotriazol-1-yl-oxytripyrrolidinophosphonium hexafluorophosphate
TEA triethylamine
TFA trifluoroacetic acid
THF tetrahydrofuran
TLC thin layer chromatography
TMS-Cl trimethylsilyl chloride

Synthesis of Precursors (E)-methyl 2-(tert-butyloxycarbonylamino)-4-(1-benzyloxycarbonyl-piperidin-4-yl)but-2-enoate

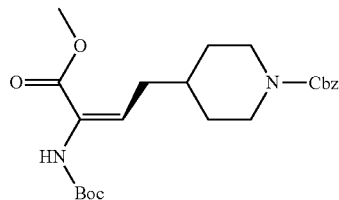

(3.1)

To a solution of Boc-α-phosphonoglycine trimethyl ester (20 g, 67 mmol) in THF (80 ml) was added 1,1,3,3-tetramethylguanidine (8 ml, 64 mmol) at −78° C. and stirring was continued for 20 min 2-(4-benzyloxycarbonyl piperidine)-acetaldehyde (16 g, 61 mmol) was added and the mixture stirred at −78° C. for 1 h and at 0° C. for 2 h. The solution was diluted with ethyl acetate, washed with aqueous 5% $KHSO_4$ and brine. The organic layer was dried ($Na_2SO_4$) and evaporated in vacuo. The residue was purified by FC using silica gel 60 (40-63 µm) and a gradient from 0-70% ethyl acetate in cyclohexane to afford the title compound.

Yield: 24.7 g (93%, white solid).

Anal. HPLC: 79.8% B; TLC: $R_f$=0.58 (PE/EE 1:1); MS calc.: 432.2. found 455.0 $(M+Na)^+$.

Boc-hAla(4-Pip[Cbz])-OMe

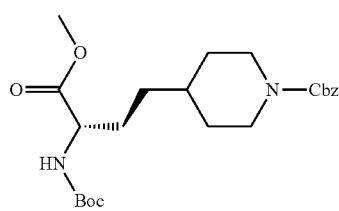

(3.2)

[Rh(COD)(S,S)-Et-duphos)]OTf (167 mg, 0.231 mmol) was placed in a 100 ml Schlenk flask previously set under argon. Degassed methanol (50 ml) was then added and the solution stirred for 5 min Compound 3.1 (10.0 g, 23.1 mmol) was placed in a 1 L Schlenk flask, dissolved in methanol (450 ml) and stirred at room temperature for 10 min Both the substrate and the catalyst solution were then transferred via canula into a 1 L stainless steel reactor previously set under argon. The reactor was sealed, purged with argon in three cycles (1 bar/20 bar) and finally, the argon replaced with hydrogen (4 cycles 1 bar/20 bar). The reactor pressure was set to 4 bar hydrogen and stirring was started. After 18.5 h, the pressure was released and the solvent evaporated in vacuo. The residue was filtered through a short pad of $SiO_2$ (20 g; ethyl acetate/n-heptane=1:3) and the solvent evaporated in vacuo to afford the title compound.

Yield: 9.7 g (97%).

Anal. HPLC: 78.1% B TLC: $R_f$=0.74 (BAE); MS calc.: 434.2. found 435.0 $(M+H)^+$.

Enantiomeric purity (ee): >99.5% (chiral HPLC)

Boc-hAla(4-Pip-[Cbz])-OH

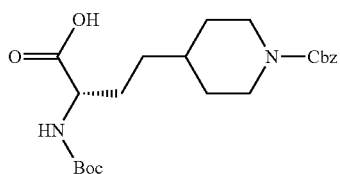

(3.3)

A mixture of methyl ester 3.2 (1.7 g, 3.9 mmol) in dioxane (10 ml) and aqueous 1 N LiOH (10 ml) was stirred at room temperature for 2 h and then neutralized by the addition of aqueous 1 N HCl. The solvent was evaporated in vacuo, the residue dissolved in ethyl acetate and the solution washed with aqueous 5% $KHSO_4$ and brine. The organic layer was dried ($Na_2SO_4$) and evaporated in vacuo to afford the title compound.

Yield: 1.65 g (97%, white solid)

Anal. HPLC: 77.1% B, TLC: $R_f$=0.4 (BAE), MS calc.: 420.2. found: 419.1 $(M-H)^-$.

Boc-hAla(4-Pip)-OMe

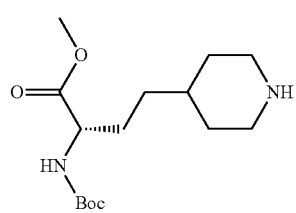

(3.4)

To a solution of compound 3.2 (2.2 g, 5 mmol) in methanol (350 ml) 10% Pd/C (20 mg) was added at room temperature under nitrogen. The nitrogen was replaced by hydrogen and the mixture stirred at room temperature for 2 h. The mixture was flushed with nitrogen, filtered through Celite™ and the solvent evaporated in vacuo to afford the title compound.

Yield: 1.5 g (99.8%, oil)

TLC: $R_f$=0.49 (4:1:1); MS calc.: 300.2. found 301.0 $(M+H)^+$.

Boc-hAla(4-Pip-[Cbz-4-$NO_2$])—OMe

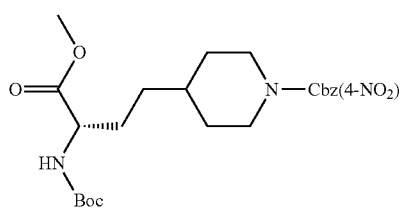

(3.5)

To a solution of compound 3.4 (1.5 g, 4.9 mmol) in THF (25 ml) was added 4-nitrobenzyloxycarbonyl-chloride (1.1 g, 4.9 mmol) and TEA (0.85 ml, 6 mmol) at room temperature and the mixture was stirred for 1.5 h while maintaining the pH of the reaction between 8-9 by addition of TEA. The solvent was evaporated in vacuo, the residue dissolved in ethyl acetate, washed with aqueous 5% $KHSO_4$ and brine. The organic layer was dried ($Na_2SO_4$) and evaporated in vacuo to afford the title compound.

Yield: 2.35 g (100%, oil).

Anal. HPLC: 76.7% B; TLC: $R_f$=0.89 (5:1); MS calc.: 479.2. found 480.0 $(M+H)^+$.

Boc-hAla(4-Pip-[Cbz-4-$NO_2$])—OH

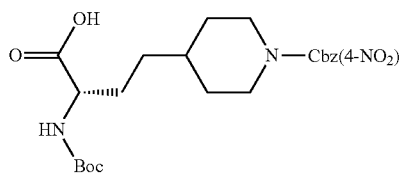

(3.6)

Compound 3.5 (2.5 g, 5.2 mmol) was converted to the title compound according to the procedure described for compound 3.3.

Yield: 2.1 g (85%)

Anal. HPLC: 73.8% B; TLC: $R_f$=0.6 (5:1); MS calc.: 465.2. found 465.9 $(M+H)^+$.

Boc-DGly(4-Pyrpren)-OH

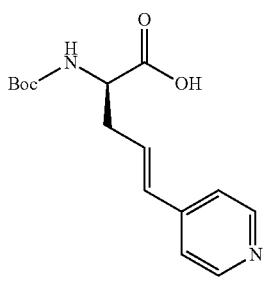

(4.1)

To a solution of Boc-allylglycine (1.65 g, 7.7 mmol) and 4-iodopyridine (1.38 g, 6.75 mmol) in DMF (40 ml) was added a solution of NaHCO$_3$ (1.7 g, 20.5 mmol) in water (20 ml) and the mixture was incubated at 70° C. for 10 min Palladium acetate (160 mg, 0.7 mmol) was added and the mixture was stirred at 70° C. for 4 h and at room temperature overnight. The catalyst was filtered off and the solvent evaporated in vacuo. Purification by FC using silica gel 60 (40-63 μm) and a gradient from 0-38% methanol in DCM afforded the title compound.

Yield: 2.1 g (94.6%, yellow solid).

Anal. HPLC: 36.1% B; TLC: $R_f$=0.45 (1:1:1:1); MS calc.: 292.1. found 292.9 (M+H)$^+$.

H-DGly(4-Pyrpr)-OH×AcOH

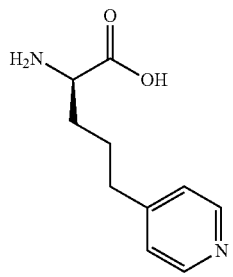

(4.2)

To a solution of compound 4.1 (5 g, 17 mmol) in 90% acetic acid (300 ml) Pd/C (500 mg) was added under argon. The argon was replaced with hydrogen and the mixture stirred at room temperature overnight. The catalyst was filtered off and the solvent evaporated in vacuo. The oily intermediate was dissolved in 1 N HCl in acetic acid (5 ml) and stirred at room temperature for 1 h. The solvent was evaporated in vacuo and the residue dissolved in a small amount of methanol. Addition of diethyl ether and filtering afforded the title compound.

Yield: 3.8 g (83.1%, white solid).

TLC: $R_f$=0.12 (1:1:1:1); MS calc.: 194.2. found 194.6 (M+H)$^+$.

Boc-DGly(4-Pippr)-OH×AcOH (AW 3-34)

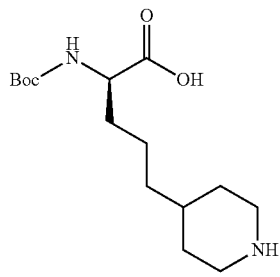

(4.3)

To a solution of compound 4.1 (2 g, 6.8 mmol) in 90% acetic acid (50 ml) and ethanol (100 ml) was added 10% Pt$_2$O (200 mg) under argon. The argon was replaced with hydrogen and the mixture stirred at room temperature overnight. The catalyst was filtered off, the solvent evaporated in vacuo and the residue dissolved in a small amount of methanol. Addition of diethyl ether and filtering afforded the title compound.

Yield: 1.5 g (62.1%, amorphous solid)

TLC: $R_f$=0.43 (1:1:1:1); MS calc.: 300.2. found 301.1 (M+H)$^+$.

H-DGly(4-Pippr[Cbz-4-NO$_2$])—OH×HCl

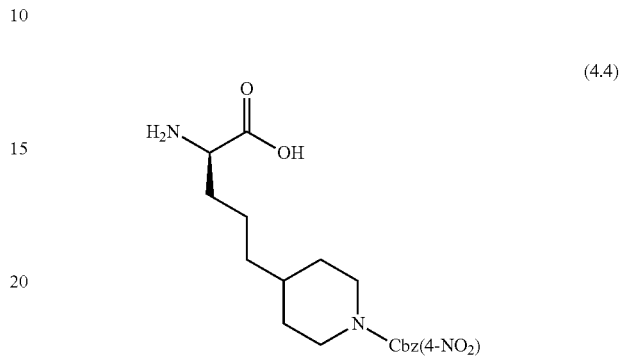

(4.4)

To a mixture of compound 4.3 (200 mg, 0.55 mmol) in aqueous 1 N NaOH (2 ml, 2 mmol), dioxane (8 ml) and water (5 ml) was added 4-nitrobenzyloxycarbonyl-chloride (120 mg, 0.55 mmol) at 0° C. with stirring. The pH was maintained at 8-9 by addition of aqueous 1M NaOH. Stirring was continued at room temperature for 2 h. The solvent was removed in vacuo and the residue portioned between ethyl acetate and aqueous 5% KHSO$_4$. The organic layer was washed with aqueous 5% KHSO$_4$ and brine, dried (Na$_2$SO$_4$), and evaporated in vacuo. The oily intermediate was dissolved in 1 N HCl in acetic acid (5 ml) and stirred at room temperature for 1 h. The solvent was evaporated in vacuo and the residue dissolved in a small amount of methanol. Addition of diethyl ether and filtering afforded the title compound.

Yield: 79 mg (41.3%, white solid).

Anal. HPLC: 55.0% B; MS calc.: 379.2. found 380.0 (M+H)$^+$.

H-DGly(Tzlpr)-OH

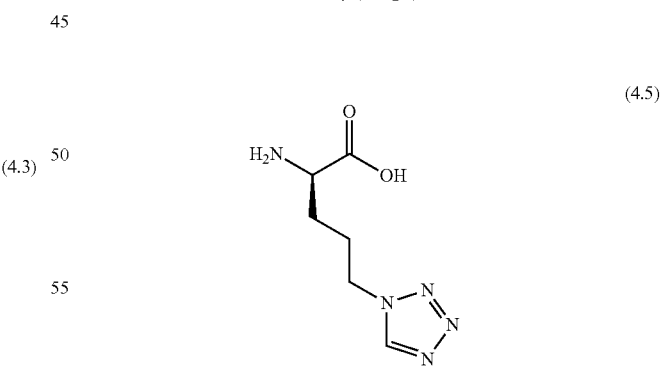

(4.5)

To a solution of Cbz-DOrn-OH (1.33 g, 5 mmol) in acetic acid (40 ml) was added sodium azide (1.5 g, 23 mmol) and trimethyl orthoformate (9.8 ml, 90 mmol) and the mixture was stirred at 80° C. for 2 h. The solvent was evaporated in vacuo and the residue dissolved in ethanol (3 ml). Aqueous 2 N NaOH was added and the mixture stirred at room temperature for 15 min. The pH of the reaction mixture was adjusted to 3 by addition of aqueous 2 N HCl followed by extraction with ethyl acetate. The organic layer was separated, dried (NaSO₄), and the solvent evaporated in vacuo. The crude intermediate was dissolved in methanol (75 ml) and ethanol (75 ml) followed by addition of 10% Pd/C (50 mg) under argon. The argon was replaced with hydrogen and the mixture was stirred at room temperature overnight. The catalyst was filtered off and washed with water. The organic solvent was evaporated in vacuo and the residue lyophilized to afford the title compound.

Yield: 740 mg (80%, white powder)
MS calc.: 185.2. found 186.1 (M+H)$^+$.

Boc-DhAla(4-Pip-[Cbz])-OMe

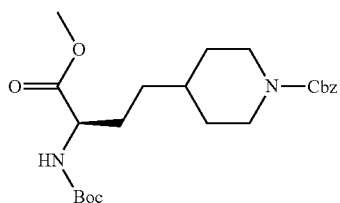
(4.6)

The title compound was prepared from compound 3.1 (10.0 g, 23.1 mmol) according to the procedure described for compound 3.2, using [Rh(COD)(R,R)-Et-duphos)]OTf as the catalyst.

Yield: 9.8 g (98%, oil)
Anal. HPLC: 78.1% B; TLC: R$_f$=0.74 (BAE); MS calc.: 434.2. found 435.0 (M+H)$^+$.
Enantiomeric purity (ee): >99.5% (chiral HPLC)

Boc-DhAla(4-Pip)-OMe

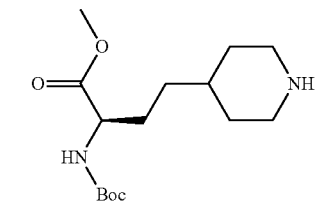
(4.7)

Compound 4.6 (3.2 g, 7.3 mmol) was converted to the title compound according to the procedure described for compound 3.4.

Yield: 2 g (92%, oil).
TLC: R$_f$=0.67 (1:1:1:1); MS calc.: 300.2. found 301.1 (M+H)$^+$.

Boc-DhAla(4-Pip-[Cbz-4-NO₂])—OMe

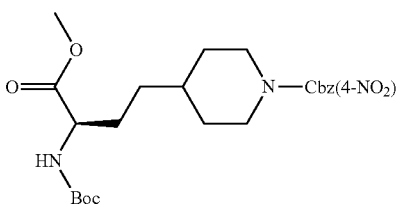
(4.8)

Compound 4.7 (2 g, 6.7 mmol) was converted to the title compound according to the procedure described for compound 3.5.

Yield: 3.2 g (100%).
Anal. HPLC: 76.5% B; TLC: MS calc.: 479.2. found 478.6 (M−H)$^-$.

H-DhAla(4-Pip-[Cbz-4-NO₂])—OMe×HCl

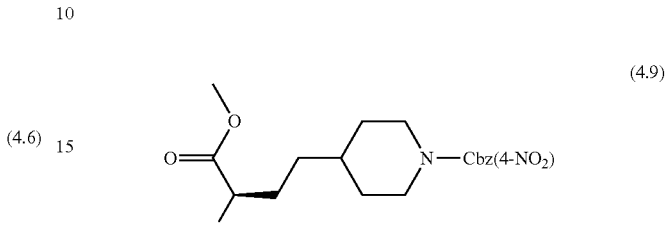
(4.9)

To a solution of compound 4.8 (3.2 g, 6.7 mmol) in acetic acid (7 ml) 1N HCl in acetic acid (15 ml) was added and the mixture stirred at room temperature for 1 h. The solvent was partially evaporated in vacuo followed by addition of diethyl ether. The solid was filtered off, washed with diethyl ether, and dried in vacuo to afford the title compound.

Yield: 2.2 g (81%, white solid).
Anal. HPLC: 52.8% B; MS calc.: 379.2. found 380.0 (M+H)$^+$.

H-hAla(4-Pip-[Cbz-4-NO₂])-4-oxadiazolon-benzyl-amide×TFA

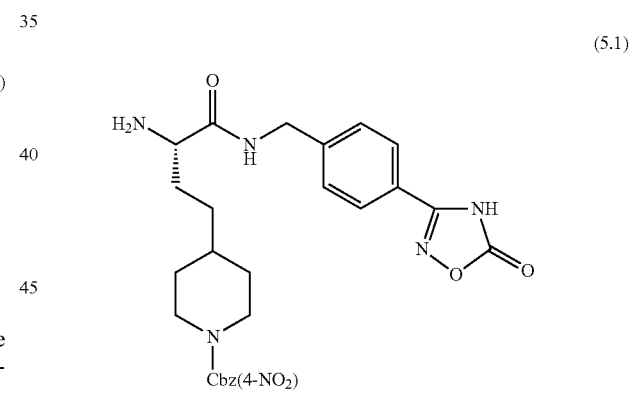
(5.1)

To a solution of compound 3.6 (1.7 g, 3.7 mmol) in DMF (10 ml) was added NMM (0.37 ml, 3.7 mmol) and isobutyl chloroformate (0.48 ml, 3.7 mmol) at −20° C. The mixture was stirred for 10 min and 3-[4-(aminomethyl)phenyl]-1,2,4-oxadiazol-5-one HCl (1.2 g, 4.1 mmol; CAS 1097196-63-8, WO/2009/005076) and NMM (0.41 ml, 4.1 mmol) was added. The mixture was stirred at −15° C. for 1 h while maintaining the pH between 8-9 by addition of NMM. The reaction mixture was stirred at room temperature overnight and the solvent evaporated in vacuo. The residue was dissolved in ethyl acetate and consecutively washed with aqueous 5% KHSO₄, saturated aqueous NaHCO₃ and brine. The organic layer was dried (Na₂SO₄) and the solvent evaporated in vacuo. The product obtained was suspended in DCM (5 ml) and TFA (3 ml) was added and the mixture was stirred at room temperature for 1 h. The solvent was partially removed in vacuo followed by addition of diethyl ether. The product was filtered off, washed with diethyl ether, and dried in vacuo to afford the title compound.

Yield: 1.8 g (74%, white solid).

Anal. HPLC: 59.2% B; MS calc.: 538.2. found 539.0 (M+H)+.

The compounds listed in Table 2 were prepared according to the procedure described for compound 5.1:

To a mixture of DPpg (3 g, 15 mmol) in aqueous 1M NaOH (15 ml, 15 mmol), dioxane (100 ml) and water (30 ml) was added in parallel a solution of Bzls-chloride (4.4 g, 23 mmol) in dioxane (10 ml) and aqueous 1M NaOH (25 ml, 25 mmol) at 0° C. over a period of 60 min. The pH was maintained between 8-9 by addition of aqueous 1M NaOH. The mixture was stirred at room temperature overnight.

TABLE 2

| # | Structure | Precursors | MS calculated/ found | Anal. HPLC % B |
|---|-----------|------------|---------------------|----------------|
| 5.2 | 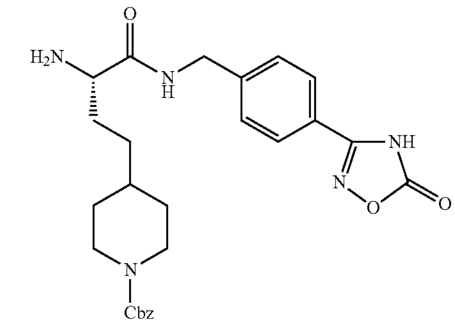 [SMILES: N[C@@H](CCC1CCN(C(=O)OCc2ccccc2)CC1)C(=O)NCc1ccc(-c2noc(=O)[nH]2)cc1] | a) 3.3 and b) CAS 1097196-63-8 | 493.5/494.1 (M + H)+ | 60.2 |
| 5.3 | 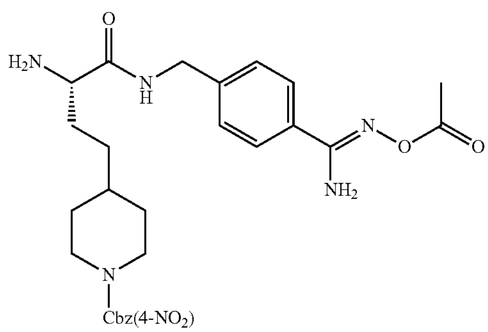 | a) 3.6 and b) CAS 380237-43-4 | 554.5/555.1 (M + H)+ | 52.8 |
| 5.4 | 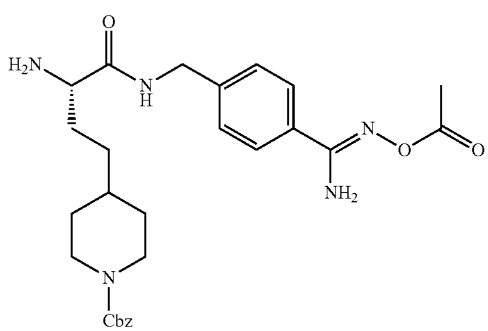 [SMILES: CC(=O)O/N=C(\N)c1ccc(CNC(=O)[C@@H](N)CCC2CCN(C(=O)OCc3ccccc3)CC2)cc1] | a) 3.3 and b) CAS 380237-43-4 | 509.6/510.1 (M + H)+ | 57.2 |

Bzls-DPpg-OH (6.1)

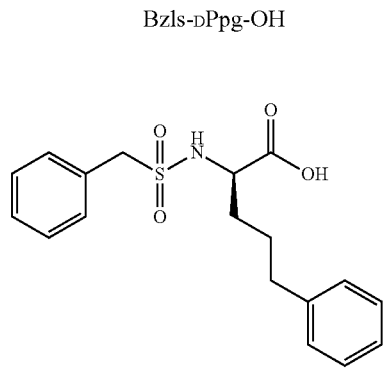

Additional Bzls-chloride (6 g, 31 mmol) and aqueous 1M NaOH (31 ml, 31 mmol) was added at 0° C. in portions and the pH maintained between 8-9 by addition of aqueous 1M NaOH. Stirring was continued until no more starting material was detected by TLC. The solvent was evaporated in vacuo and the residue portioned between ethyl acetate and aqueous 5% KHSO$_4$. The organic layer was washed with aqueous 5% KHSO$_4$ and brine, dried (Na$_2$SO$_4$), and evaporated in vacuo to afford the title compound.

Yield: 4 g (75%, white solid).

Anal. HPLC: 69.3% B; MS calc.: 347.1. found 346.3 (M−H)−.

(3-MeOOC)Bzls-DPpg-OH

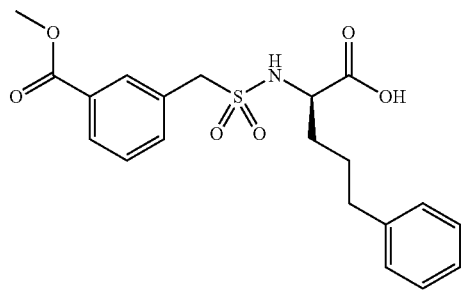

(6.2)

To a suspension of DPpg (1.3 g, 6.7 mmol) in dry DCM (90 ml) was added TMS-Cl (2 ml, 15.7 mmol) and DIEA (2.6 ml, 15 mmol) at room temperature and the mixture was refluxed for 1 h with stirring. The clear solution was cooled to 0° C. and (3-MeOOC)Bzls-chloride (2 g, 8 mmol) and DIEA (2.6 ml) was added. The mixture was stirred at 0° C. for 15 min and at room temperature for 1.5 h. The solvent was evaporated in vacuo and the residue dissolved in half-saturated aqueous NaHCO$_3$ (700 ml) followed by extraction with ethyl acetate. The aqueous layer was acidified with aqueous HCl (pH about 2-3) and extracted with ethyl acetate. The organic layer was washed with aqueous 5% KHSO$_4$ and brine, dried (Na$_2$SO$_4$), and evaporated in vacuo to afford the title compound.

Yield: 2.4 g (88%, amorphous yellow solid).

Anal. HPLC: 69.2 min % B; MS calc.: 405.1. found 404.3 (M−H)$^-$.

The compounds listed in Table 3 were prepared according to the procedure described for compound 6.1 or 6.2:

TABLE 3

| # | Structure | Precursors/ remarks | MS calculated/ found | Anal. HPLC % B |
|---|---|---|---|---|
| 6.3 | 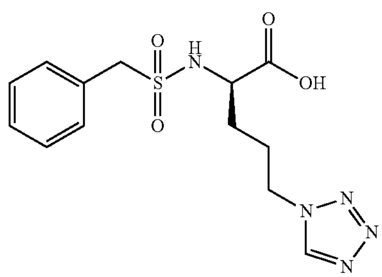 [SMILES: O=C(O)[C@@H](CCCn1cnnn1)NS(=O)(=O)Cc1ccccc1] | Synthesized according to the procedure described for compound 6.1 using: a) Bzls-Cl and b) 4.5 | 339.1/ 340.2 (M + H)$^+$ | 38.6 |
| 6.4 | 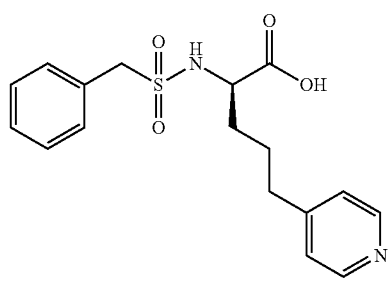 [SMILES: O=C(O)[C@@H](CCCc1ccncc1)NS(=O)(=O)Cc1ccccc1] | Synthesized according to the procedure described for compound 6.1 using: a) Bzls-Cl and b) 4.2 purification by FC | 348.1/ 348.9 (M + H)$^+$ | 33.6 |
| 6.5 | 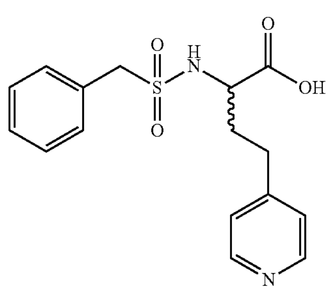 [SMILES: O=C(O)C(CCc1ccncc1)NS(=O)(=O)Cc1ccccc1] | Synthesized according to the procedure described for compound 6.1 using: a) Bzls-Cl and b) D,LhAla(4-Pyr) purification by FC | 334.1/ 334.9 (M − H)$^-$ | 31.2 |

TABLE 3-continued

| # | Structure | Precursors/remarks | MS calculated/found | Anal. HPLC % B |
|---|---|---|---|---|
| 6.6 | 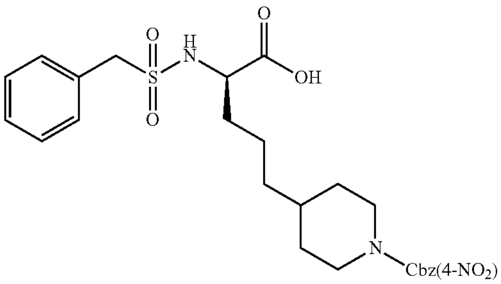 | Synthesized according to the procedure described for compound 6.1 using:<br>a) Bzls-Cl and<br>b) 4.4 | 519.2/<br>520.0<br>(M + H)⁺ | 75.9 |
| 6.7 | 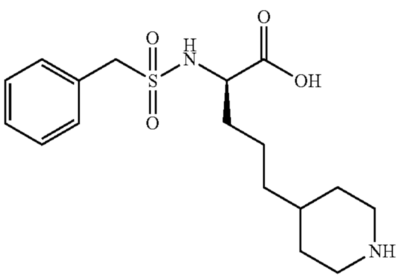 [SMILES: O=C(O)[C@@H](CCCC1CCNCC1)NS(=O)(=O)Cc1ccccc1] | 6.6 was hydrogenated according to the procedure described for compound 3.4 | 354.2/<br>355.0<br>(M + H)⁺ | 35.7 |
| 6.8 | 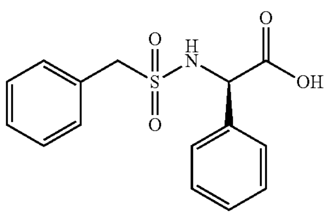 [SMILES: O=C(O)[C@H](NS(=O)(=O)Cc1ccccc1)c1ccccc1] | Synthesized according to the procedure described for compound 6.2 using:<br>a) Bzls-Cl and<br>b) DPhg | 305.1/<br>306.2<br>(M + H)⁺ | 64.1 |

Bzls-DhAla(4-Pip[Cbz-4-NO₂])—OH (6.9)

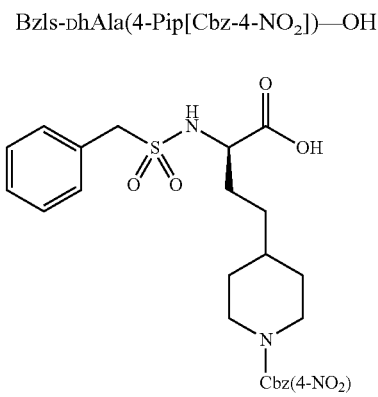

To a solution of compound 4.9 (2.2 g, 5.3 mmol) and DIEA (2 ml, 11.7 mmol) in DMF (40 ml) was added Bzls-chlorid (1.1 g, 5.8 mmol) at 0° C. with stirring and the pH was maintained between 8-9 by addition of DIEA. The mixture was stirred at room temperature overnight and the solvent evaporated in vacuo. The residue was portioned between ethyl acetate and aqueous 5% KHSO₄, the organic layer was washed with aqueous 5% KHSO₄ and brine, dried (Na₂SO₄) and evaporated in vacuo. The main part of the residue obtained was used for the synthesis of compound 6.10. A remaining part of the residue (100 mg) was hydrolyzed according to the procedure described for compound 3.3 to afford the title compound.

Yield: 80 mg
Anal. HPLC: 73.9% B; MS calc.: 519.2. found 520.0 (M+H)⁺.

Bzls-DhAla(4-Pip)-OMe (6.10)

Hydrogenolysis of the main part of residue 6.9 was done according to the procedure described for compound 3.4 and in the presence aqueous 1N HCl (5 ml). The residue was dissolved in a small amount of methanol. Addition of diethyl ether and filtering afforded the title compound.

Yield: 2.3 g (>100%, light red solid)
Anal. HPLC: 39.8% B; MS calc.: 354.2. found 355.0 (M+H)⁺.

Crude 6.10 was used for further reactions with acid chlorides, isocyanates or anhydrides, e.g. as described for compound 6.11 and summarized in Table 4 below.

Bzls-dhAla(4-Pip[CO-Et])-OH (6.11)

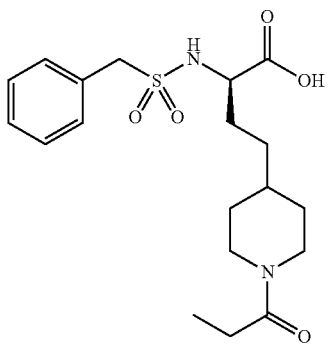

To a solution of compound 6.10 (100 mg, 0.21 mmol) and DIEA (0.08 ml, 0.46 mmol) in THF (5 ml) was added propionyl-chloride (0.02 ml, 0.23 mmol) at 0° C. with stirring and the pH was maintained between 8-9 by addition of DIEA. The mixture was stirred at room temperature for 3 h and the solvent evaporated in vacuo. The residue was portioned between ethyl acetate and 5% KHSO$_4$-solution. The organic layer was washed with aqueous 5% KHSO$_4$ and brine, dried (Na$_2$SO$_4$) and evaporated in vacuo. The title compound was obtained by hydrolysis of the crude intermediate according to the procedure described for compound 3.3.

Yield: 74 mg (88%, oil)

Anal. HPLC: 59.3% B, MS calc.: 396.5. found 397.3 (M+H)$^+$.

TABLE 4

| # | Structure | precursors/ remarks | MS calculated/ found | Anal. HPLC % B |
|---|---|---|---|---|
| 6.12 | 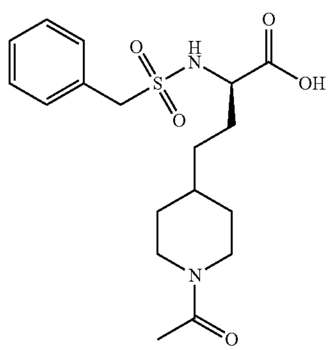 [SMILES: CC(=O)N1CCC(CC[C@@H](NS(=O)(=O)Cc2ccccc2)C(=O)O)CC1] | a) 6.10 and b) acetic anhydride | 382.2/381.0 (M − H)$^−$ | 60.2 |
| 6.13 | 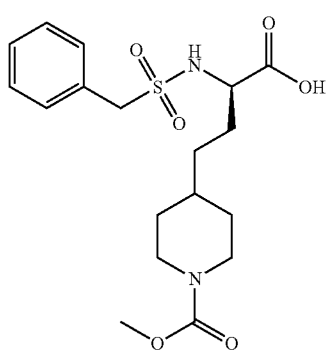 [SMILES: COC(=O)N1CCC(CC[C@@H](NS(=O)(=O)Cc2ccccc2)C(=O)O)CC1] | a) 6.10 and b) methyl chloroformate | 398.1/396.9 (M − H)$^−$ | 58.3 |
| 6.14 | 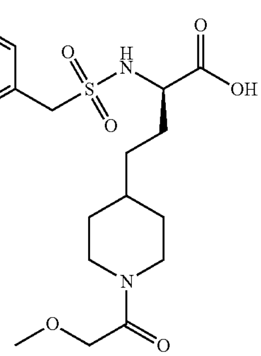 | a) 6.10 and b) methoxyacetyl chloride | 412.1/411.1 (M − H)$^−$ | 54.1 |

TABLE 4-continued

| # | Structure | precursors/ remarks | MS calculated/ found | Anal. HPLC % B |
|---|---|---|---|---|
| 6.15 | 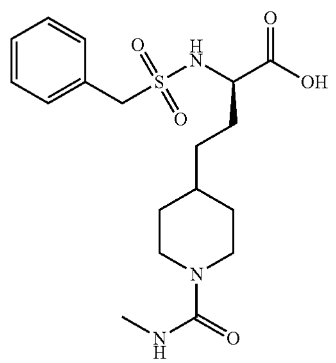 [SMILES: CNC(=O)N1CCC(CC[C@@H](NS(=O)(=O)Cc2ccccc2)C(=O)O)CC1] | a) 6.10 and b) methyl isocyanate | 397.2/398.2 (M + H)+ | 55.3 |
| 6.16 | 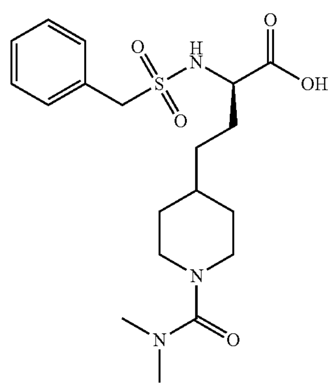 [SMILES: CN(C)C(=O)N1CCC(CC[C@@H](NS(=O)(=O)Cc2ccccc2)C(=O)O)CC1] | a) 6.10 and b) dimethylcarbamoyl chloride | 411.2/409.9 (M − H)− | 57.2 |
| 6.17 | 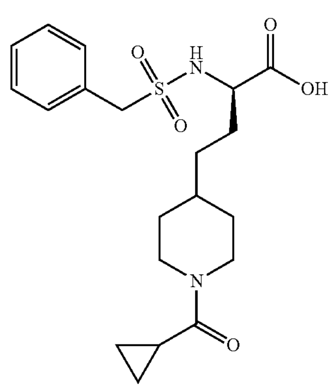 [SMILES: O=C(O)[C@@H](CCC1CCN(C(=O)C2CC2)CC1)NS(=O)(=O)Cc1ccccc1] | a) 6.10 and b) cyclopropanecarbonyl chloride | 408.2/ 409.1 (M + H)+ | 57.3 |
| 6.18 | 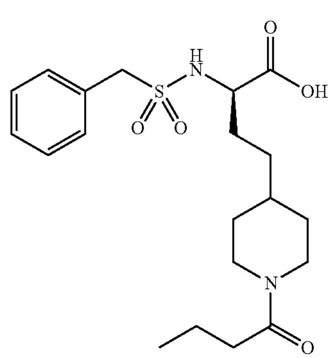 [SMILES: CCCC(=O)N1CCC(CC[C@@H](NS(=O)(=O)Cc2ccccc2)C(=O)O)CC1] | a) 6.10 and b) butanoyl chloride | 410.2/409.1 (M − H)− | 63.7 |

TABLE 4-continued

| # | Structure | precursors/ remarks | MS calculated/ found | Anal. HPLC % B |
|---|---|---|---|---|
| 6.19 | 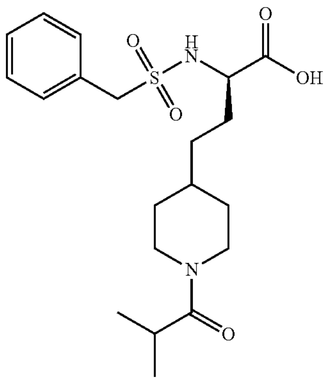 [SMILES: CC(C)C(=O)N1CCC(CC[C@@H](NS(=O)(=O)Cc2ccccc2)C(=O)O)CC1] | a) 6.10 and b) isobutanoyl chloride | 410.2/411.1 (M + H)⁺ | 61.2 |
| 6.20 | 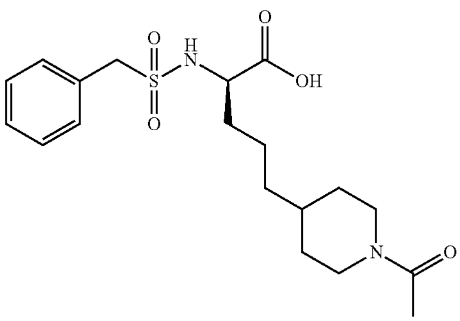 [SMILES: CC(=O)N1CCC(CCC[C@@H](NS(=O)(=O)Cc2ccccc2)C(=O)O)CC1] | a) 6.7 and b) acetic anhydride | 396.2/397.1 (M + H)⁺ | 63.8 |
| 6.21 | 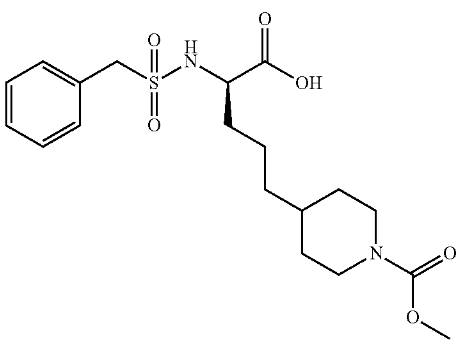 [SMILES: COC(=O)N1CCC(CCC[C@@H](NS(=O)(=O)Cc2ccccc2)C(=O)O)CC1] | a) 6.7 and b) methyl chloroformiate | 411.4/412.2 (M − H)⁻ | 71.1 |

Synthesis of the Inhibitors

Bzls-DPpg-hAla(4-Pip)-4-Ambax2TFA (1.1)

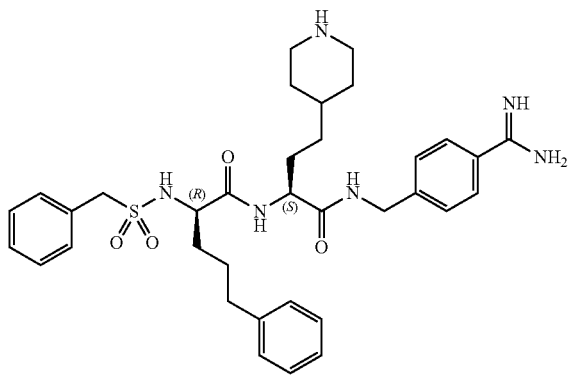

To a solution of compound 6.1 (160 mg, 0.46 mmol) and compound 5.2 (280 mg, 0.46 mmol) in dry DMF (4 ml) was added PyBop (265 mg, 0.5 mmol) and DIEA (220 µl, 1.2 mmol) at 0° C. The mixture was stirred at 0° C. for 15 min and at room temperature for 1.5 h. The solvent was evaporated in vacuo, the residue dissolved in ethyl acetate and consecutively washed with aqueous 5% KHSO$_4$, saturated aqueous NaHCO$_3$, and brine. The organic layer was dried (Na$_2$SO$_4$) and the solvent evaporated in vacuo. The crude intermediate was dissolved in 90% acetic acid (80 ml) and 10% Pd/C (50 mg) was added under nitrogen. The nitrogen was replaced with hydrogen and the mixture stirred at room temperature overnight. The catalyst was filtered off and the solvent evaporated in vacuo. 1 N HBr in acetic acid (3 ml) was added and the mixture stirred at room temperature for 1 h. Diethyl ether was added, the crude product was isolated by filtration and purified by reversed phase HPLC. Lyophilization afforded the title compound.

Yield: 125 mg (31%, white powder)

Anal. HPLC: 54.7% B; MS calc.: 646.3. found 647.2 (M+H)+.

Bzls-DGly(4-Pyrpr)-hAla(4-Pip)-4-Amba×3TFA (1.2)

Bzls-DGly(4-Pyrpr[NO])-hAla(4-Pip)-4-Amba× 2TFA (1.8)

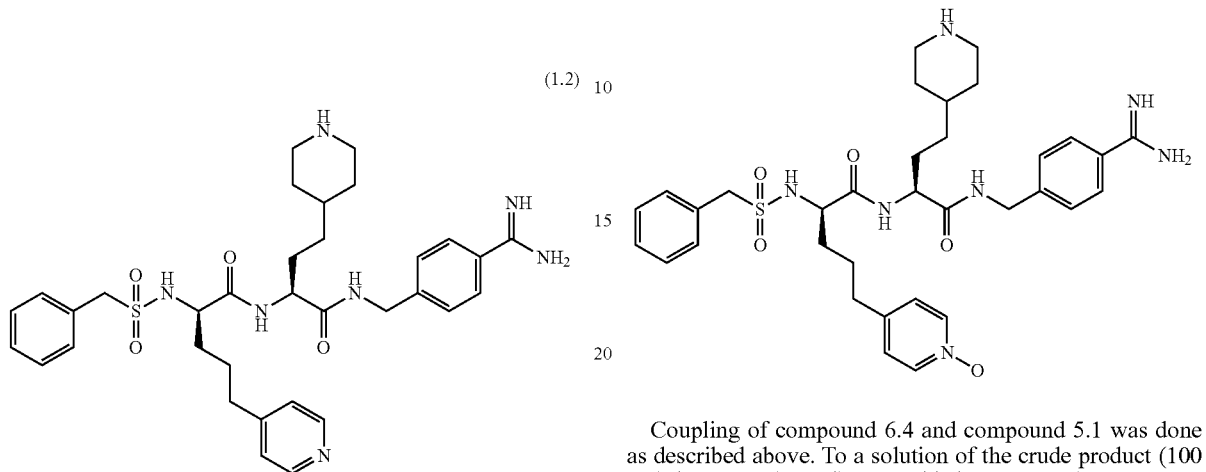

Coupling of compound 6.4 (260 mg, 0.56 mmol) and compound 5.1 (365 mg, 0.56 mmol) was done according the procedure described for compound 1.1. The crude intermediate was obtained after treatment with saturated aqueous NaHCO₃ and filtration. Hydrogenolysis according to the procedure described for compound 1.1 afforded the title compound Yield: 215 mg (39%, white powder)

Anal. HPLC: 31.6 min % B; MS calc.: 647.3. found 648.1 (M+H)+.

Coupling of compound 6.4 and compound 5.1 was done as described above. To a solution of the crude product (100 mg) in DCM (10 ml) was added m-CPBA (27 mg, 0.15 mmol) and the mixture was stirred at room temperature for 4 h. Additional m-CPBA (15 mg, 0.075 mmol) was added and stirring was continued for 1 h. Aqueous 39% sodium hydrogen sulphite (0.2 ml) was added and the solvent was evaporated in vacuo. The residue was dissolved in ethyl acetate and washed with saturated aqueous NaHCO₃ and brine. The organic layer was dried (Na₂SO₄) and the solvent evaporated in vacuo. The protected intermediate was hydrogenated and purified according the procedure described for 1.1. The crude product was isolated by filtration and purified by reversed phase HPLC. Lyophilization afforded the title compound.

Yield: 7 mg

Anal. HPLC: 33.4 min % B; MS calc.: 663.3. found 664.1 (M+H)+.

The compounds listed in Table 5 were prepared according to the procedure described for compound 1.1:

TABLE 5

| # | Structure | precursors/ remarks | MS calculated/ found | HPLC % B |
|---|---|---|---|---|
| 1.7 | 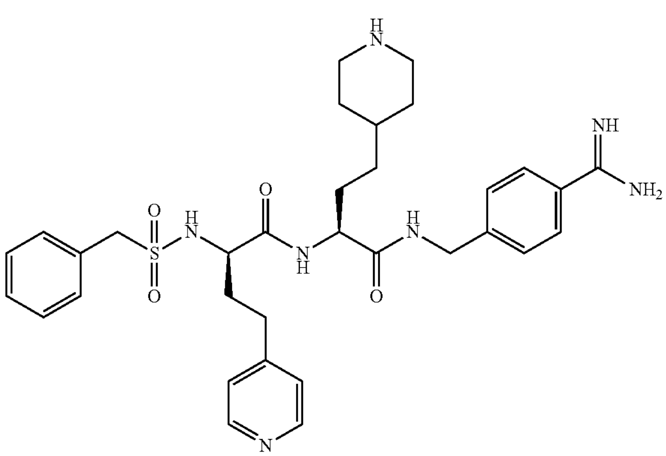 [SMILES: N=C(N)c1ccc(CNC(=O)[C@H](CCC2CCNCC2)NC(=O)[C@@H](CCc2ccncc2)NS(=O)(=O)Cc2ccccc2)cc1] | a) 5.1 and b) 6.5 Diastereomers were separated by preparative HPLC | 633.3/634.1 (M + H)+ | 29.7 |

TABLE 5-continued

| # | Structure | precursors/ remarks | MS calculated/ found | HPLC % B |
|---|---|---|---|---|
| 1.9 | 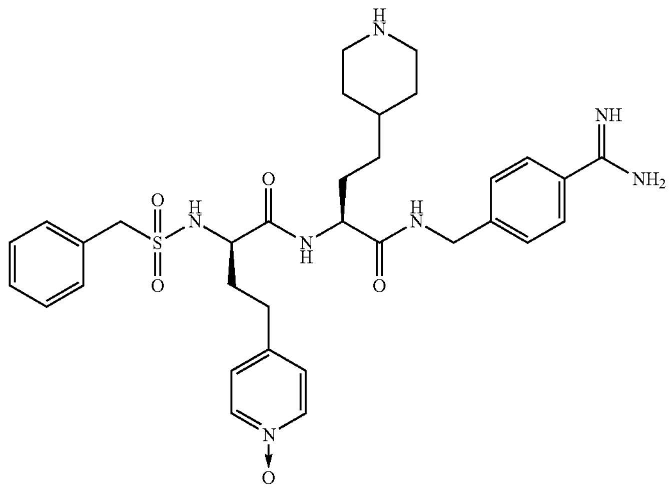 [SMILES: N=C(N)c1ccc(CNC(=O)[C@H](CCC2CCNCC2)NC(=O)[C@@H](CCc2cc[n+]([O-])cc2)NS(=O)(=O)Cc2ccccc2)cc1] | Synthesized from compound 1.7 according to procedure described for compound 1.8 | 649.3/650.1 (M + H) | 31.2 |
| 1.4 | 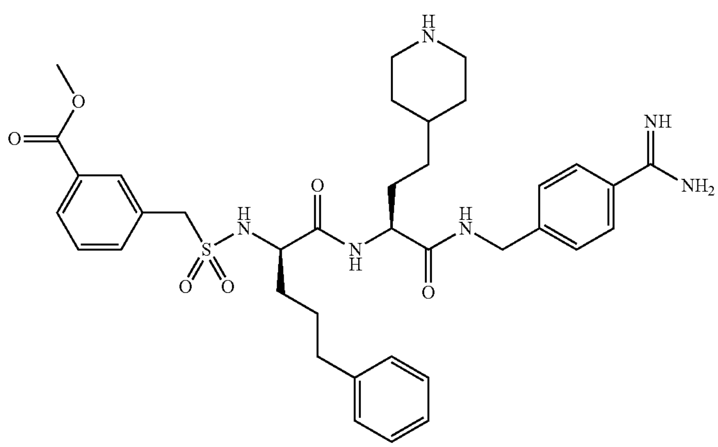 [SMILES: COC(=O)c1cccc(CS(=O)(=O)N[C@H](CCCc2ccccc2)C(=O)N[C@@H](CCC2CCNCC2)C(=O)NCc2ccc(C(=N)N)cc2)c1] | a) 5.1 and b) 6.2 | 704.3/705.2 (M + H)+ | 51.5 |
| 1.3 | 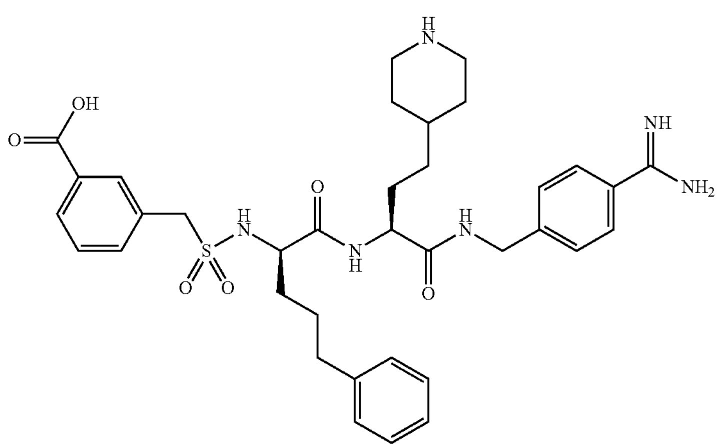 [SMILES: N=C(N)c1ccc(CNC(=O)[C@H](CCC2CCNCC2)NC(=O)[C@@H](CCCc2ccccc2)NS(=O)(=O)Cc2cccc(C(=O)O)c2)cc1] | Compound 1.4 was hydrolyzed according to procedure described for compound 3.3 | 690.3/691.2 (M + H)+ | 47.1 |

TABLE 5-continued

| # | Structure | precursors/ remarks | MS calculated/ found | HPLC % B |
|---|---|---|---|---|
| 1.5 | 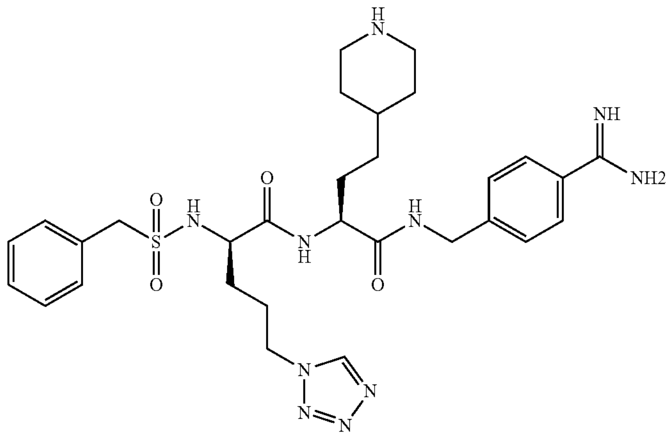 [SMILES: N=C(N)c1ccc(CNC(=O)[C@H](CCC2CCNCC2)NC(=O)[C@@H](CCCn2cnnn2)NS(=O)(=O)Cc2ccccc2)cc1] | a) 5.1 and b) 6.3 | 638.3/639.1 (M + H)+ | 37.1 |
| 1.6 | 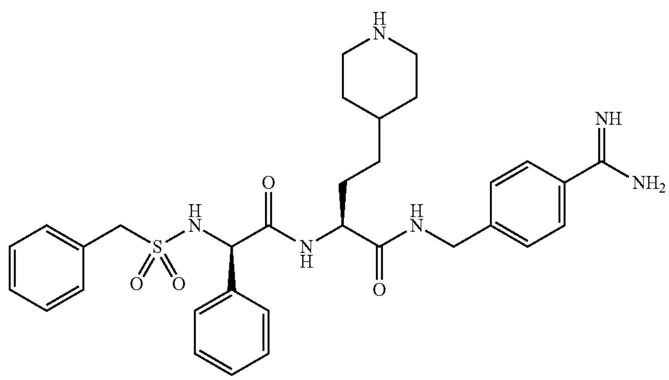 [SMILES: N=C(N)c1ccc(CNC(=O)[C@H](CCC2CCNCC2)NC(=O)[C@H](NS(=O)(=O)Cc2ccccc2)c2ccccc2)cc1] | a) 5.1 and b) 6.8 | 604.7/605.2 (M + H)+ | 41.9 |
| 2.9 | 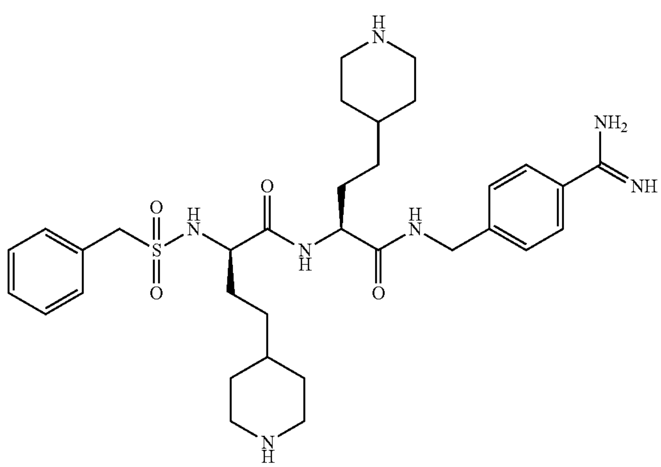 [SMILES: N=C(N)c1ccc(CNC(=O)[C@H](CCC2CCNCC2)NC(=O)[C@@H](CCC2CCNCC2)NS(=O)(=O)Cc2ccccc2)cc1] | a) 5.3 and b) 6.9 | 639.4/640.2 (M + H)+ | 34.1 |

TABLE 5-continued
| # | Structure | precursors/ remarks | MS calculated/ found | HPLC % B |
|---|---|---|---|---|
| 2.1 | 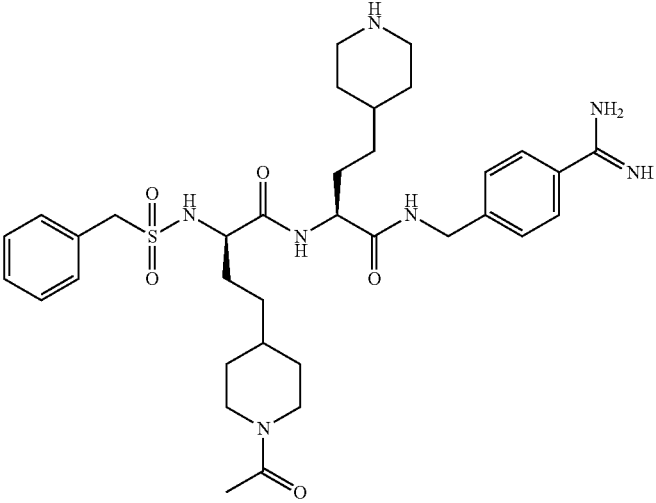 [SMILES: CC(=O)N1CCC(CC[C@@H](NS(=O)(=O)Cc2ccccc2)C(=O)N[C@@H](CCC2CCNCC2)C(=O)NCc2ccc(C(=N)N)cc2)CC1] | a) 5.4 and b) 6.12 | 681.4/682.1 (M + H)+ | 43.3 |
| 2.2 | 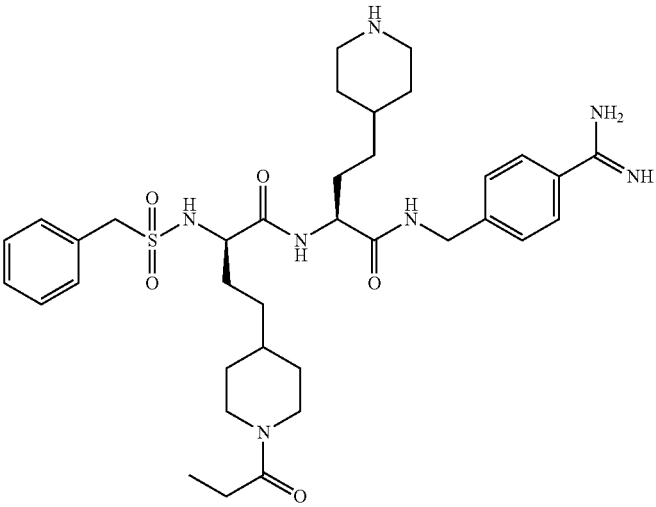 [SMILES: CCC(=O)N1CCC(CC[C@@H](NS(=O)(=O)Cc2ccccc2)C(=O)N[C@@H](CCC2CCNCC2)C(=O)NCc2ccc(C(=N)N)cc2)CC1] | a) 5.3 and b) 6.11 | 695.8/696.2 (M + H)+ | 46.4 |
| 2.3 | 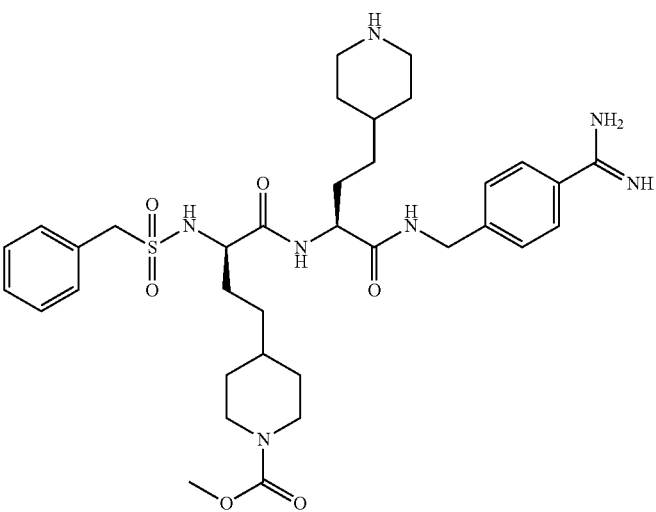 [SMILES: COC(=O)N1CCC(CC[C@@H](NS(=O)(=O)Cc2ccccc2)C(=O)N[C@@H](CCC2CCNCC2)C(=O)NCc2ccc(C(=N)N)cc2)CC1] | a) 5.1 and b) 6.13 | 697.4/698.2 (M + H)+ | 44.7 |

TABLE 5-continued
| # | Structure | precursors/ remarks | MS calculated/ found | HPLC % B |
|---|---|---|---|---|
| 2.4 | 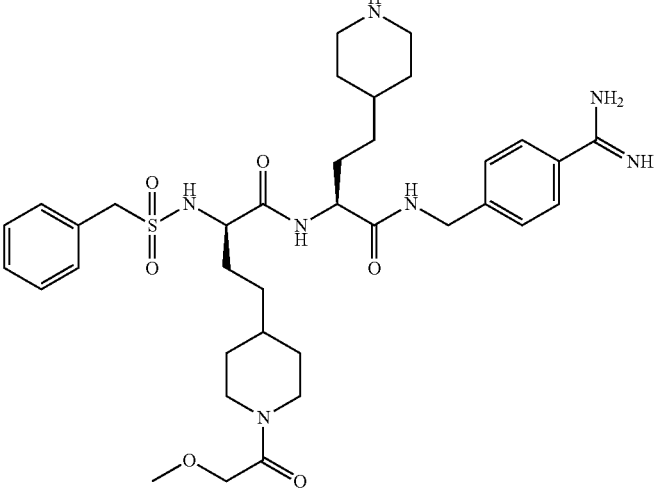 | a) 5.3 and b) 6.14 | 711.4/712.4 (M + H)+ | 43.4 |
| 2.5 | 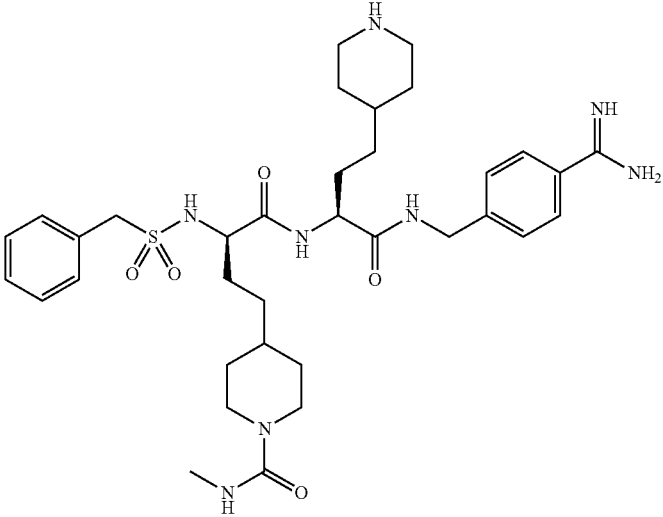 [SMILES: CNC(=O)N1CCC(CC[C@@H](NS(=O)(=O)Cc2ccccc2)C(=O)N[C@@H](CCC2CCNCC2)C(=O)NCc2ccc(C(=N)N)cc2)CC1] | a) 5.1 and b) 6.15 | 696.4/697.7 (M + H)+ | 42.6 |
| 2.6 | 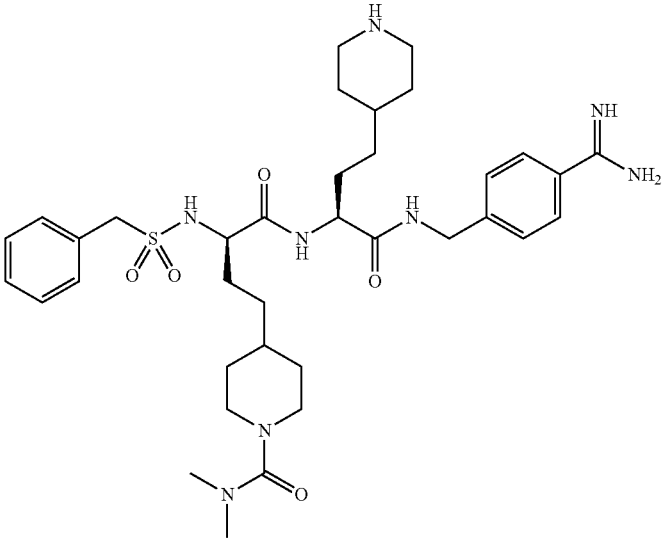 [SMILES: CN(C)C(=O)N1CCC(CC[C@@H](NS(=O)(=O)Cc2ccccc2)C(=O)N[C@@H](CCC2CCNCC2)C(=O)NCc2ccc(C(=N)N)cc2)CC1] | a) 5.1 and b) 6.16 | 710.4/711.2 (M + H)+ | 43.4 |

TABLE 5-continued
| # | Structure | precursors/ remarks | MS calculated/ found | HPLC % B |
|---|---|---|---|---|
| 2.10 | 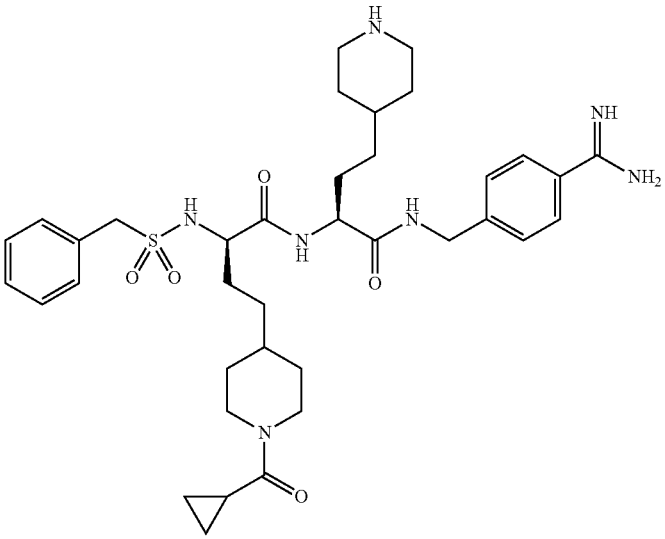 [SMILES: N=C(N)c1ccc(CNC(=O)[C@H](CCC2CCNCC2)NC(=O)[C@@H](CCC2CCN(C(=O)C3CC3)CC2)NS(=O)(=O)Cc2ccccc2)cc1] | a) 5.3 and b) 6.17 | 707.4/708.2 (M + H)+ | 44.5 |
| 2.12 | 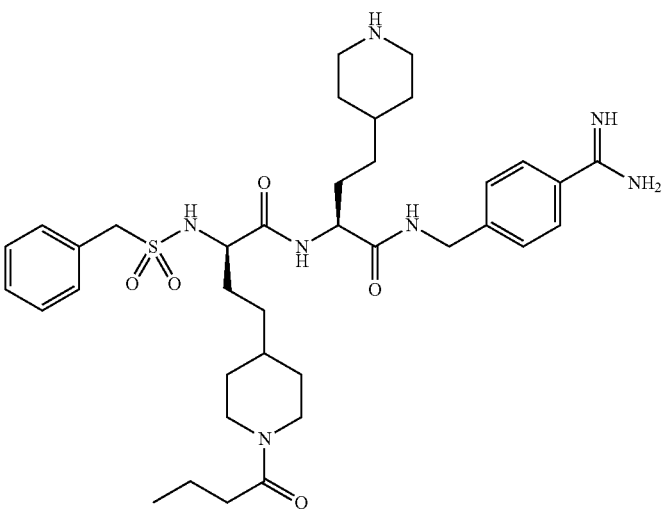 [SMILES: CCCC(=O)N1CCC(CC[C@@H](NS(=O)(=O)Cc2ccccc2)C(=O)N[C@@H](CCC2CCNCC2)C(=O)NCc2ccc(C(=N)N)cc2)CC1] | a) 5.3 and b) 6.18 | 709.4/710.2 (M + H)+ | 50.1 |

TABLE 5-continued
| # | Structure | precursors/ remarks | MS calculated/ found | HPLC % B |
|---|---|---|---|---|
| 2.11 | 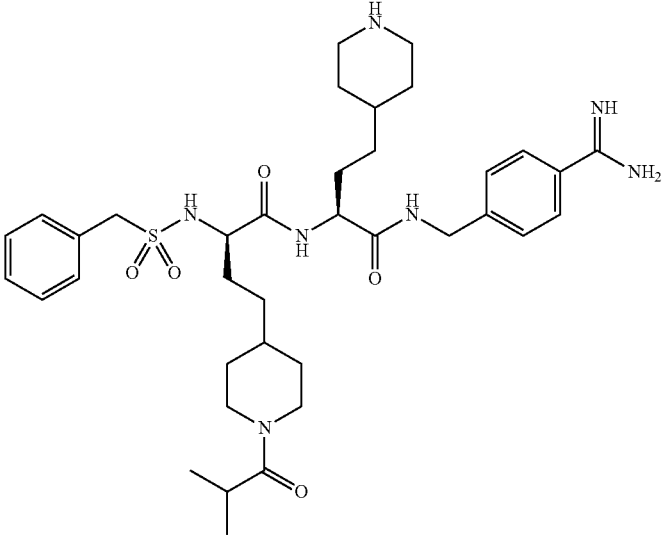 [SMILES: CC(C)C(=O)N1CCC(CC[C@@H](NS(=O)(=O)Cc2ccccc2)C(=O)N[C@@H](CCC2CCNCC2)C(=O)NCc2ccc(C(=N)N)cc2)CC1] | a) 5.2 and b) 6.19 | 709.4/701.2 (M + H)+ | 50.5 |
| 2.8 | 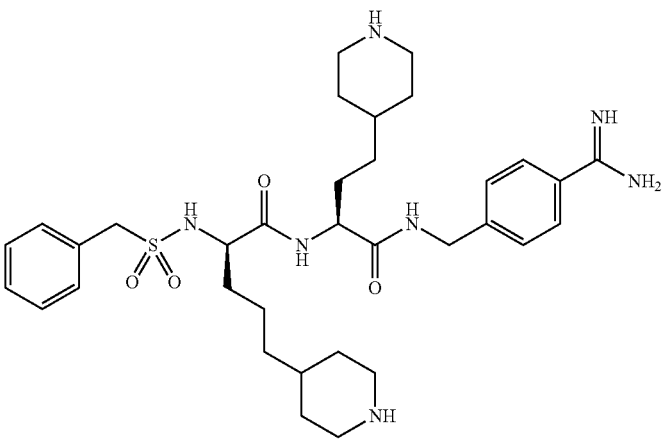 [SMILES: N=C(N)c1ccc(CNC(=O)[C@H](CCC2CCNCC2)NC(=O)[C@@H](CCCC2CCNCC2)NS(=O)(=O)Cc2ccccc2)cc1] | a) 5.3 and b) 6.6 | 653.4/645.3 (M + H)+ | 35.8 |
| 2.7 | 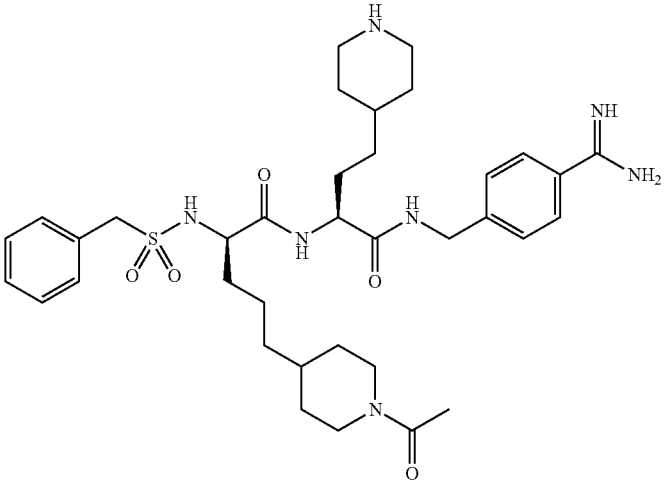 [SMILES: CC(=O)N1CCC(CCC[C@@H](NS(=O)(=O)Cc2ccccc2)C(=O)N[C@@H](CCC2CCNCC2)C(=O)NCc2ccc(C(=N)N)cc2)CC1] | a) 5.3 and b) 6.20 | 695.4/696.0 (M + H)+ | 45.7 |

TABLE 5-continued

| # | Structure | precursors/ remarks | MS calculated/ found | HPLC % B |
|---|---|---|---|---|
| 2.13 | 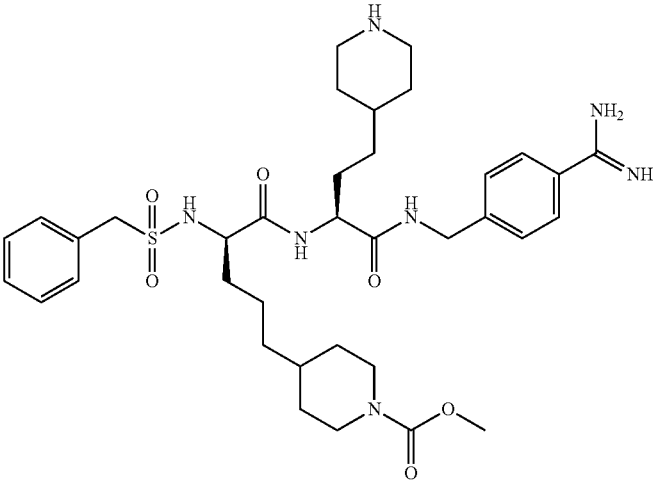 [SMILES: COC(=O)N1CCC(CCC[C@@H](NS(=O)(=O)Cc2ccccc2)C(=O)N[C@@H](CCC2CCNCC2)C(=O)NCc2ccc(C(=N)N)cc2)CC1] | a) 5.3 and b) 6.21 | 711.4/712.2 (M + H)+ | 52.8 |

Determination of the Inhibition Constants for Human Plasmin (h Plasmin) and Human Plasma Kallikrein (h PK)

The inhibitory effect for the individual enzymes was determined in analogy to a previously disclosed method (Stürzebecher et al., *J. Med. Chem.*, 40, 3091-3099 (1997)). The reactions to determine the inhibition of human plasmin and human plasma kallikrein were carried out in the following mixture at 25° C.:

200 µl of TBS (0.05 M trishydroxymethylaminomethane; 0.154 M NaCl, 2% ethanol, pH 8.0)

25 µl of substrate (4 mM, 2 mM and 1 mM tosyl-Gly-Pro-Lys-pNA=Chromozym PL from LOXO for plasmin and 3 mM, 1.5 mM and 1 mM H-D-Pro-Phe-Arg-pNA=S2302 from Chromogenix for PK, dissolved in H$_2$O)

2 µL of a test compound solution in 50% v/v DMSO/water

50 µl of enzyme solution (plasmin from Calbiochem: 1.7 mU/ml in 0.154 M NaCl+0.1% BSA m/v; plasma kallikrein from Enzyme Research Lab.: 62 ng/ml in 0.154 M NaCl+ 0.1% BSA m/v)

For zero order kinetics, the reaction was stopped after 20 mM by adding 15 µl of acetic acid (80% v/v), and the absorption at 405 nm was determined using a Microplate Reader (Multiscan Ascent™, from Thermo). In the case of pseudo-first order kinetics, the reaction rates in the equilibrium state were determined by continuously recording the change in absorbance at 405 nm. The $K_i$ values were calculated by parameter fitting in accordance with the rate equation for competitive inhibition using the GraFit software, version 4. The $K_i$ values are the average of at least three determinations.

Determination of Inhibition Constants for Reference Enzymes

Human Activated Protein C (h aPC): Inhibition of human aPC was determined by the method described in [0092]-[0098] using human activated protein C from Enzyme Research Laboratories at 2.2 nM and H-D-Lys(Cbo)-Pro-Arg-pNA (Pefachrome PCa) at 2 mM, 1 mM, and 0.5 mM as substrate; results are reported as Ki values (nanomolar).

Human urinary kallikrein (h uKK): Inhibition of human uKK was determined by the method described in [0092]-[0098] using human urinary kallikrein from Lee Biosolutions at 7.5 nM and H-D-Val-Leu-Arg-pNA (S-2266) at 1 mM, 0.5 mM, and 0.25 mM as substrate; results are reported as Ki values (nanomolar).

Subcomponent "s" of Human Complement Component 1 (h C1s): Inhibition of human C1s was determined by the method described in [0092]-[0098] using native human activated C1s complement component from Calbiochem at 29 nM and Val-Ser-Arg-pNA (S2314) at 8 mM, 6 mM, and 4 mM as substrate; results are reported as Ki values (nanomolar).

Subcomponent "r" of Human Complement Component 1 (h C1r): Inhibition of human C1r was determined by the method described in [0092]-[0098] using native human activated C1r complement component from Calbiochem at 100 nM and Val-Ser-Arg-pNA (S2314) at 16 mM, 12 mM, and 8 mM as substrate; results are reported as Ki values (nanomolar).

Human Factor IIa (h FIIa): Inhibition of human FIIa was determined by the method described in [0092]-[0098] using human alpha-thrombin from Enzyme Research Laboratories at 0.1 NIH U/mL and Mes-d-Cha-Gly-Arg-pNA (Pefachrome tPA) at 2 mM, 1 mM, and 0.5 mM as substrate; results are reported as Ki values (nanomolar).

Human Factor Xa (h FXa): Inhibition of human FXa was determined by the method described in [0092]-[0098] using activated human Factor X from Enzyme Research Laboratories at 5 mIU/mL and MeOCO-d-Cha-Gly-Arg-pNA (Pefachrome FXa) at 2 mM, 1 mM, and 0.5 mM as substrate; results are reported as Ki values (nanomolar).

Human Factor XIa (h FXIa): Inhibition of human FXIa was determined by the method described in [0092]-[0098] using activated human Factor XI from Enzyme Research Laboratories at 96 ng/mL and H-D-Lys(Cbo)-Pro-Arg-pNA (Pefachrome PCa) at 5 mM, 4 mM, and 2 mM as substrate; results are reported as Ki values (nanomolar).

Human Factor XIIa (h FXIIa): Inhibition of human alpha-FXIIa was determined by the method described in [0092]-[0098] using activated human alpha-Factor XII (activated Hageman Factor) from Enzyme Research Laboratories at 50 mPEU/mL and CHA-Gly-Arg-pNA at 2 mM, 1 mM, and 0.5 mM as substrate; results are reported as Ki values (nanomolar).

Human tissue-type plasminogen activator (h t-PA): Inhibition of human t-PA was determined by the method described in [0092]-[0098] using recombinant human tissue-type plasminogen activator (Actilyse®) from Boehringer Ingelheim at 290 U/mL and Mes-d-Cha-Gly-Arg-pNA (Pefachrome tPA) at 4 mM, 2 mM, and 1 mM as substrate; results are reported as Ki values (nanomolar).

Results for exemplary compounds of the invention are shown in Table 6.

TABLE 6

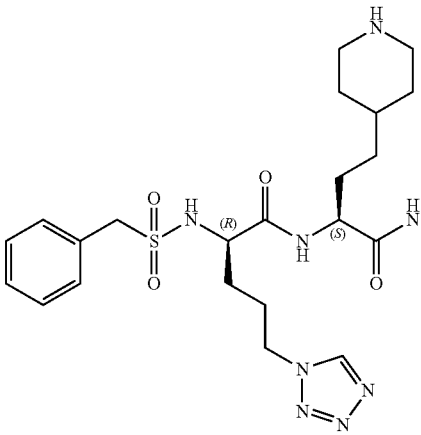

| | | |
|---|---|---:|
| h plasmin | Ki; nM | 8 |
| h PK | Ki; nM | 5.3 |
| h aPC | Ki; nM | 1,300 |
| h uKK | Ki; nM | >200,000 |
| h C1s | Ki; nM | >10,000 |
| h C1r | Ki; nM | n.d. |
| h FIIa | Ki; nM | 4,700 |
| h FXa | Ki; nM | 2,400 |
| h FXIa | Ki; nM | 1,400 |
| h FXIIa | Ki; nM | n.d. |
| h t-PA | Ki; nM | n.d. |

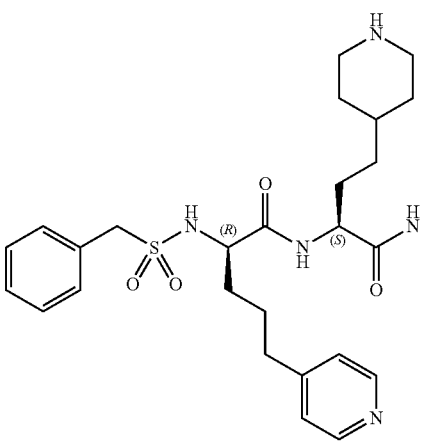

| | | |
|---|---|---:|
| h plasmin | Ki; nM | 0.4 |
| h PK | Ki; nM | 2.7 |
| h aPC | Ki; nM | 600 |
| h uKK | Ki; nM | >80,000 |
| h C1s | Ki; nM | 4,950 |
| h C1r | Ki; nM | >50,000 |
| h FIIa | Ki; nM | 1,200 |
| h FXa | Ki; nM | 850 |
| h FXIa | Ki; nM | 500 |
| h FXIIa | Ki; nM | 1,500 |
| h t-PA | Ki; nM | 2,300 |

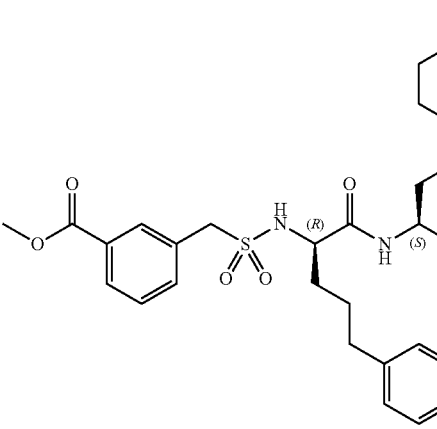

| | | |
|---|---|---:|
| h plasmin | Ki; nM | 2.7 |
| h PK | Ki; nM | 9.4 |
| h aPC | Ki; nM | 570 |
| h uKK | Ki; nM | >20,000 |
| h C1s | Ki; nM | 4,800 |
| h C1r | Ki; nM | >30,000 |
| h FIIa | Ki; nM | 920 |
| h FXa | Ki; nM | 5,900 |
| h FXIa | Ki; nM | 500 |
| h FXIIa | Ki; nM | >10,000 |
| h t-PA | Ki; nM | 3,900 |

TABLE 6-continued

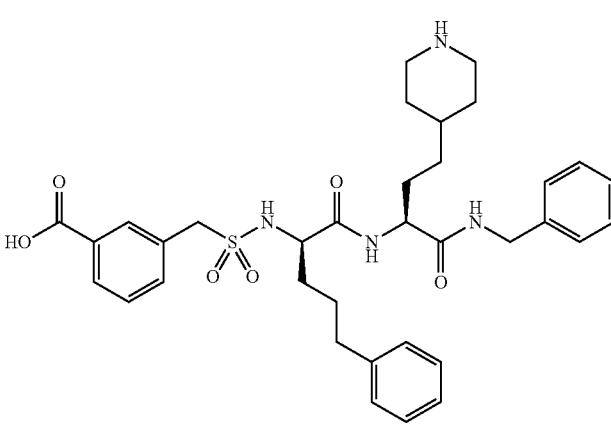

| | | |
|---|---|---|
| h plasmin | Ki; nM | 3.8 |
| h PK | Ki; nM | 3 |
| h aPC | Ki; nM | 310 |
| h uKK | Ki; nM | >20,000 |
| h C1s | Ki; nM | 1,200 |
| h C1r | Ki; nM | >20,000 |
| h FIIa | Ki; nM | 4,400 |
| h FXa | Ki; nM | 2,400 |
| h FXIa | Ki; nM | 70 |
| h FXIIa | Ki; nM | n.d. |
| h t-PA | Ki; nM | n.d. |

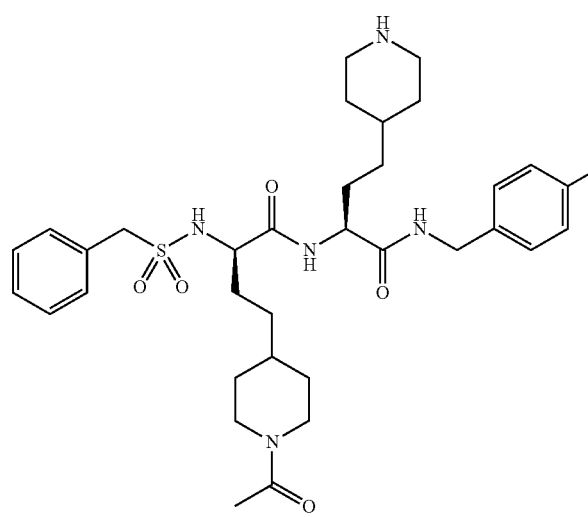

| | | |
|---|---|---|
| h plasmin | Ki; nM | 1.8 |
| h PK | Ki; nM | 5 |
| h aPC | Ki; nM | 1,200 |
| h uKK | Ki; nM | >20,000 |
| h C1s | Ki; nM | >20,000 |
| h C1r | Ki; nM | >40,000 |
| h FIIa | Ki; nM | 8,000 |
| h FXa | Ki; nM | 1,900 |
| h FXIa | Ki; nM | 1,400 |
| h FXIIa | Ki; nM | 530 |
| h t-PA | Ki; nM | 4,800 |

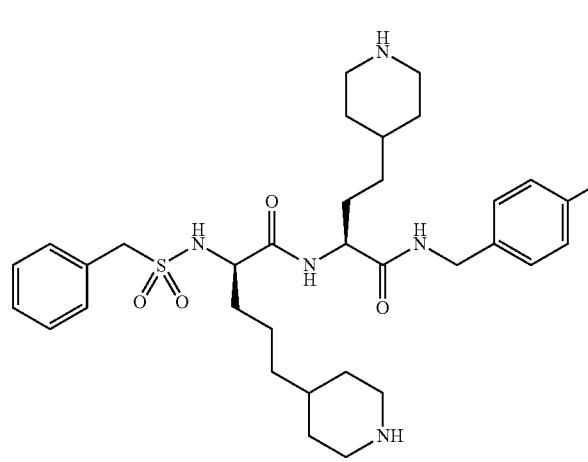

| | | |
|---|---|---|
| h plasmin | Ki; nM | 2 |
| h PK | Ki; nM | 7.5 |
| h aPC | Ki; nM | 400 |
| h uKK | Ki; nM | >50,000 |
| h C1s | Ki; nM | 8,000 |
| h C1r | Ki; nM | >50,000 |
| h FIIa | Ki; nM | 800 |
| h FXa | Ki; nM | 300 |
| h FXIa | Ki; nM | 800 |
| h FXIIa | Ki; nM | n.d. |
| h t-PA | Ki; nM | n.d. |

TABLE 6-continued
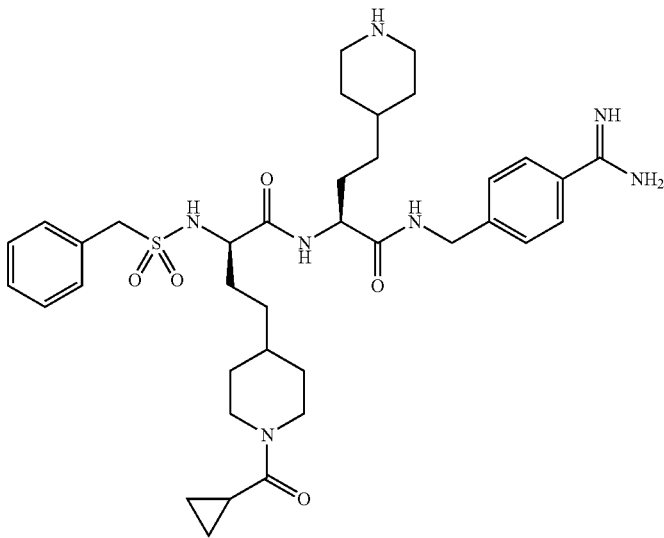 [SMILES: N=C(N)c1ccc(CNC(=O)[C@H](CCC2CCNCC2)NC(=O)[C@@H](CCC2CCN(C(=O)C3CC3)CC2)NS(=O)(=O)Cc2ccccc2)cc1]
| h plasmin | Ki; nM | 0.6 |
| h PK | Ki; nM | 0.3 |
| h aPC | Ki; nM | 1,500 |
| h uKK | Ki; nM | >50,000 |
| h C1s | Ki; nM | 19,000 |
| h C1r | Ki; nM | >50,000 |
| h FIIa | Ki; nM | 8,500 |
| h FXa | Ki; nM | 2,300 |
| h FXIa | Ki; nM | 650 |
| h FXIIa | Ki; nM | 1,100 |
| h t-PA | Ki; nM | 6,100 |
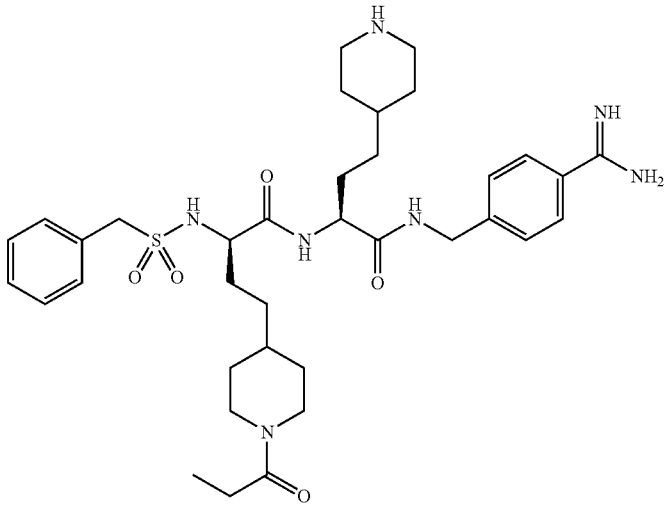 [SMILES: CCC(=O)N1CCC(CC[C@@H](NS(=O)(=O)Cc2ccccc2)C(=O)N[C@@H](CCC2CCNCC2)C(=O)NCc2ccc(C(=N)N)cc2)CC1]
| h plasmin | Ki; nM | 0.8 |
| h PK | Ki; nM | 0.9 |
| h aPC | Ki; nM | 1,200 |
| h uKK | Ki; nM | >60,000 |
| h C1s | Ki; nM | >25,000 |
| h C1r | Ki; nM | >35,000 |
| h FIIa | Ki; nM | 5,600 |
| h FXa | Ki; nM | 2,300 |
| h FXIa | Ki; nM | 720 |
| h FXIIa | Ki; nM | 650 |
| h t-PA | Ki; nM | 5,100 |
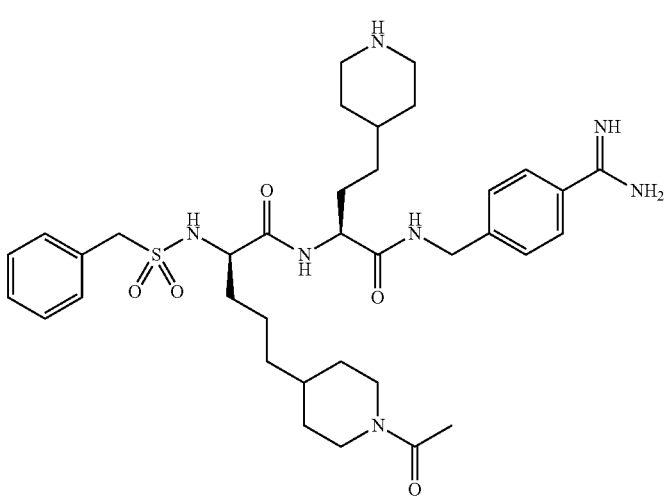 [SMILES: CC(=O)N1CCC(CCC[C@@H](NS(=O)(=O)Cc2ccccc2)C(=O)N[C@@H](CCC2CCNCC2)C(=O)NCc2ccc(C(=N)N)cc2)CC1]
| h plasmin | Ki; nM | 1.5 |
| h PK | Ki; nM | 2 |
| h aPC | Ki; nM | 1,100 |
| h uKK | Ki; nM | >500,000 |
| h C1s | Ki; nM | 9,000 |
| h C1r | Ki; nM | >100,000 |
| h FIIa | Ki; nM | 3,800 |
| h FXa | Ki; nM | 750 |
| h FXIa | Ki; nM | 870 |
| h FXIIa | Ki; nM | 630 |
| h t-PA | Ki; nM | 3,000 |

TABLE 6-continued

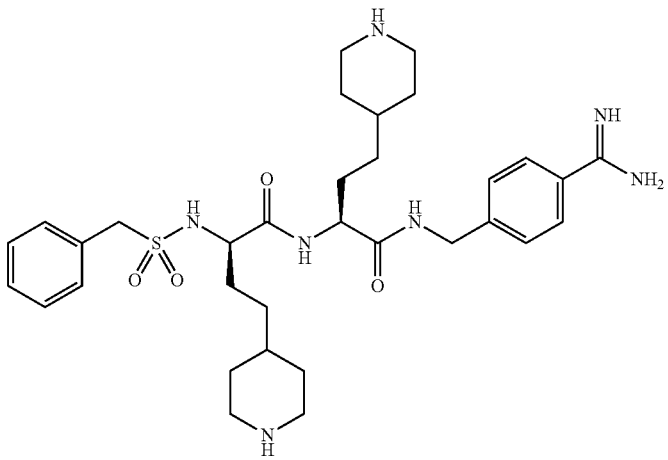 [SMILES: N=C(N)c1ccc(CNC(=O)[C@H](CCC2CCNCC2)NC(=O)[C@@H](CCC2CCNCC2)NS(=O)(=O)Cc2ccccc2)cc1]

| | | |
|---|---|---:|
| h plasmin | Ki; nM | 3 |
| h PK | Ki; nM | 7.5 |
| h aPC | Ki; nM | 60 |
| h uKK | Ki; nM | >100,000 |
| h C1s | Ki; nM | >25,000 |
| h C1r | Ki; nM | >100,000 |
| h FIIa | Ki; nM | 4,200 |
| h FXa | Ki; nM | 90 |
| h FXIa | Ki; nM | 1,400 |
| h FXIIa | Ki; nM | n.d. |
| h t-PA | Ki; nM | n.d. |

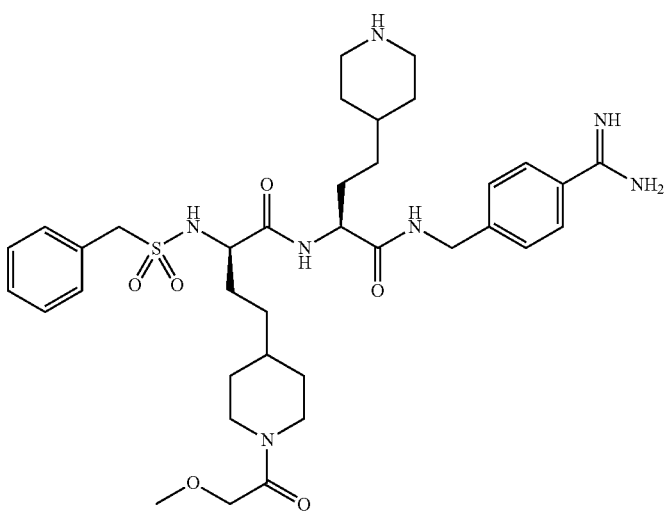 [SMILES: COCC(=O)N1CCC(CC[C@@H](NS(=O)(=O)Cc2ccccc2)C(=O)N[C@@H](CCC2CCNCC2)C(=O)NCc2ccc(C(=N)N)cc2)CC1]

| | | |
|---|---|---:|
| h plasmin | Ki; nM | 1.2 |
| h PK | Ki; nM | 1.3 |
| h aPC | Ki; nM | 1,200 |
| h uKK | Ki; nM | >100,000 |
| h C1s | Ki; nM | 20,000 |
| h C1r | Ki; nM | >50,000 |
| h FIIa | Ki; nM | 4,500 |
| h FXa | Ki; nM | 1,600 |
| h FXIa | Ki; nM | 1,400 |
| h FXIIa | Ki; nM | 680 |
| h t-PA | Ki; nM | 4,700 |

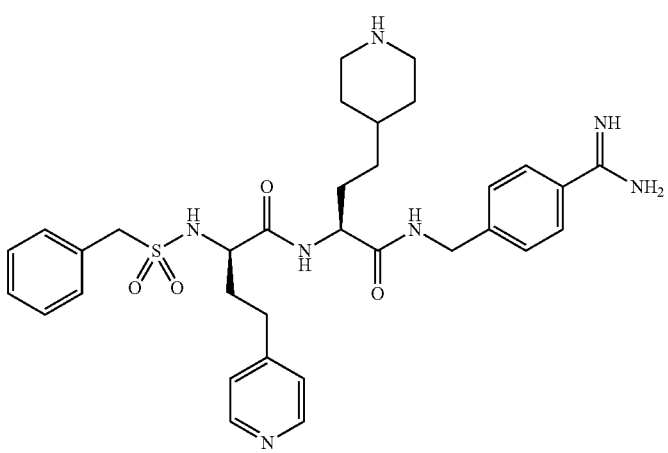 [SMILES: N=C(N)c1ccc(CNC(=O)[C@H](CCC2CCNCC2)NC(=O)[C@@H](CCc2ccncc2)NS(=O)(=O)Cc2ccccc2)cc1]

| | | |
|---|---|---:|
| h plasmin | Ki; nM | 1.5 |
| h PK | Ki; nM | 9 |
| h aPC | Ki; nM | 27 |
| h uKK | Ki; nM | >200,000 |
| h C1s | Ki; nM | 2,000 |
| h C1r | Ki; nM | >20,000 |
| h FIIa | Ki; nM | 3,900 |
| h FXa | Ki; nM | 20 |
| h FXIa | Ki; nM | 500 |
| h FXIIa | Ki; nM | n.d. |
| h t-PA | Ki; nM | n.d. |

TABLE 6-continued

| | | |
|---|---|---:|
| h plasmin | Ki; nM | 0.8 |
| h PK | Ki; nM | 4 |
| h aPC | Ki; nM | 1,600 |
| h uKK | Ki; nM | >200,000 |
| h C1s | Ki; nM | 13,000 |
| h C1r | Ki; nM | >50,000 |
| h FIIa | Ki; nM | 13,000 |
| h FXa | Ki; nM | 2,500 |
| h FXIa | Ki; nM | 1,500 |
| h FXIIa | Ki; nM | 2,000 |
| h t-PA | Ki; nM | 8,300 |

| | | |
|---|---|---:|
| h plasmin | Ki; nM | 1 |
| h PK | Ki; nM | 2 |
| h aPC | Ki; nM | 1,100 |
| h uKK | Ki; nM | >200,000 |
| h C1s | Ki; nM | >20,000 |
| h C1r | Ki; nM | >20,000 |
| h FIIa | Ki; nM | 4,800 |
| h FXa | Ki; nM | 1,700 |
| h FXIa | Ki; nM | 1,300 |
| h FXIIa | Ki; nM | 550 |
| h t-PA | Ki; nM | 5,300 |

| | | |
|---|---|---:|
| h plasmin | Ki; nM | 0.6 |
| h PK | Ki; nM | 2 |
| h aPC | Ki; nM | 1,100 |
| h uKK | Ki; nM | >200,000 |
| h C1s | Ki; nM | >10,000 |
| h C1r | Ki; nM | >15,000 |
| h FIIa | Ki; nM | 5,500 |
| h FXa | Ki; nM | 2,200 |
| h FXIa | Ki; nM | 870 |
| h FXIIa | Ki; nM | 800 |
| h t-PA | Ki; nM | 6,100 |

TABLE 6-continued
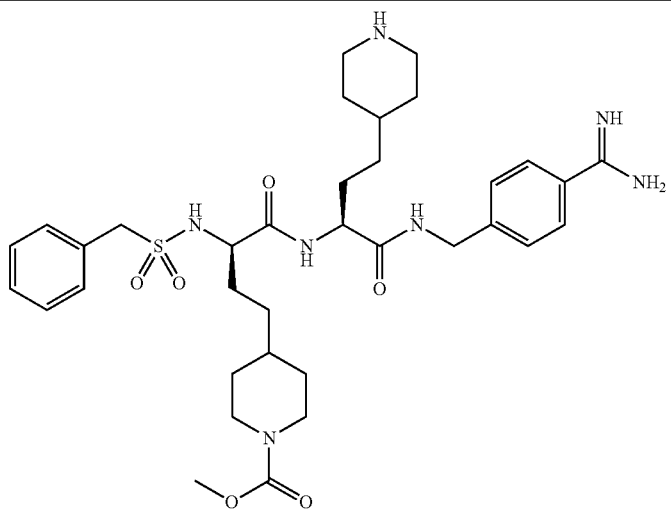
| | | |
|---|---|---|
| h plasmin | Ki; nM | 0.7 |
| h PK | Ki; nM | 2 |
| h aPC | Ki; nM | 1,350 |
| h uKK | Ki; nM | >200,000 |
| h C1s | Ki; nM | >10,000 |
| h C1r | Ki; nM | >20,000 |
| h FIIa | Ki; nM | 13,000 |
| h FXa | Ki; nM | 2,000 |
| h FXIa | Ki; nM | 720 |
| h FXIIa | Ki; nM | 1,600 |
| h t-PA | Ki; nM | 6,600 |
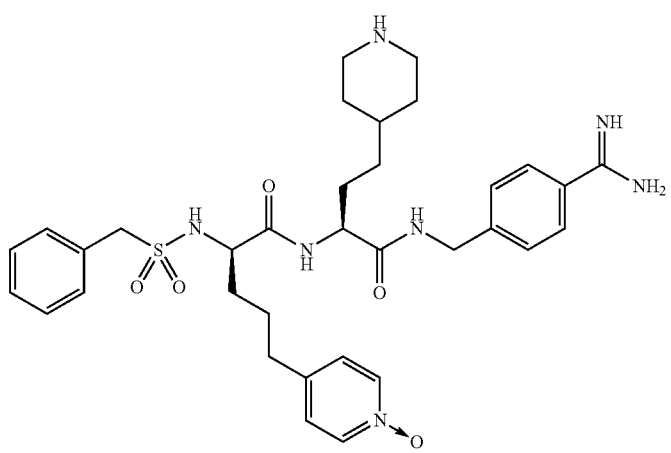 [SMILES: N=C(N)c1ccc(CNC(=O)[C@H](CCC2CCNCC2)NC(=O)[C@@H](CCCc2cc[n+]([O-])cc2)NS(=O)(=O)Cc2ccccc2)cc1]
| | | |
|---|---|---|
| h plasmin | Ki; nM | 1 |
| h PK | Ki; nM | 4 |
| h aPC | Ki; nM | 850 |
| h uKK | Ki; nM | >200,000 |
| h C1s | Ki; nM | 10,000 |
| h C1r | Ki; nM | >30,000 |
| h FIIa | Ki; nM | 4,900 |
| h FXa | Ki; nM | 400 |
| h FXIa | Ki; nM | 1,400 |
| h FXIIa | Ki; nM | 870. |
| h t-PA | Ki; nM | 2,400 |
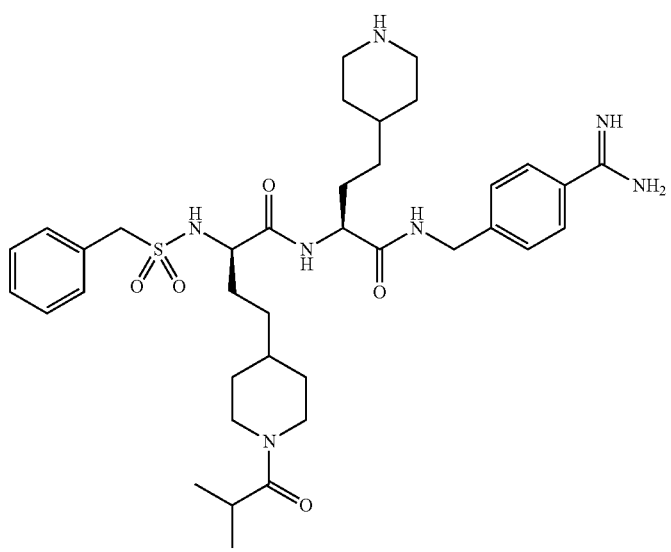 [SMILES: CC(C)C(=O)N1CCC(CC[C@@H](NS(=O)(=O)Cc2ccccc2)C(=O)N[C@@H](CCC2CCNCC2)C(=O)NCc2ccc(C(=N)N)cc2)CC1]
| | | |
|---|---|---|
| h plasmin | Ki; nM | 0.6 |
| h PK | Ki; nM | 1.5 |
| h aPC | Ki; nM | 1,700 |
| h uKK | Ki; nM | >200,000 |
| h C1s | Ki; nM | >25,000 |
| h C1r | Ki; nM | >30,000 |
| h FIIa | Ki; nM | 13,000 |
| h FXa | Ki; nM | 3,200 |
| h FXIa | Ki; nM | 920 |
| h FXIIa | Ki; nM | 1,300 |
| h t-PA | Ki; nM | 6,500 |

TABLE 6-continued

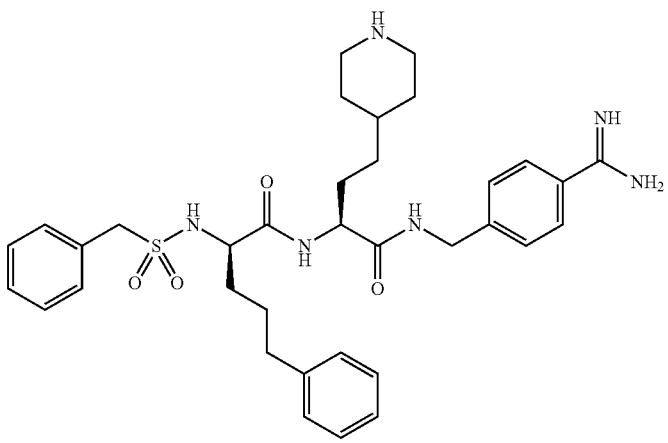 [SMILES: N=C(N)c1ccc(CNC(=O)[C@H](CCC2CCNCC2)NC(=O)[C@@H](CCCc2ccccc2)NS(=O)(=O)Cc2ccccc2)cc1]

| h plasmin | Ki; nM | 0.25 |
| h PK | Ki; nM | 1.5 |
| h aPC | Ki; nM | 555 |
| h uKK | Ki; nM | >50,000 |
| h C1s | Ki; nM | >5,000 |
| h C1r | Ki; nM | n.d. |
| h FIIa | Ki; nM | 240 |
| h FXa | Ki; nM | 1,100 |
| h FXIa | Ki; nM | 135 |
| h FXIIa | Ki; nM | 3,000 |
| h t-PA | Ki; nM | 1,700 |

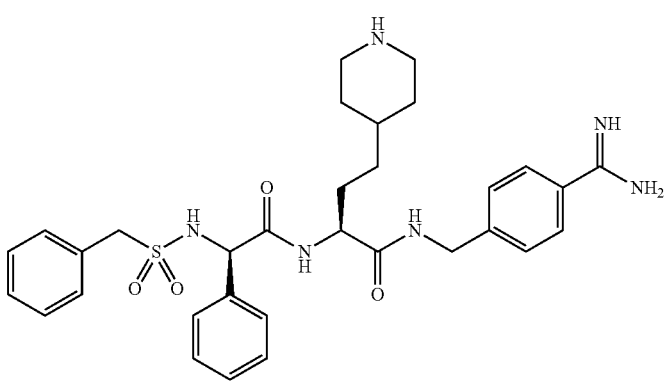 [SMILES: N=C(N)c1ccc(CNC(=O)[C@H](CCC2CCNCC2)NC(=O)[C@H](NS(=O)(=O)Cc2ccccc2)c2ccccc2)cc1]

| h plasmin | Ki; nM | 2.2 |
| h PK | Ki; nM | 20 |
| h aPC | Ki; nM | 210 |
| h uKK | Ki; nM | n.d. |
| h C1s | Ki; nM | n.d. |
| h C1r | Ki; nM | n.d. |
| h FIIa | Ki; nM | 1,700 |
| h FXa | Ki; nM | 1,600 |
| h FXIa | Ki; nM | 1,000 |
| h FXIIa | Ki; nM | n.d. |
| h t-PA | Ki; nM | n.d. |

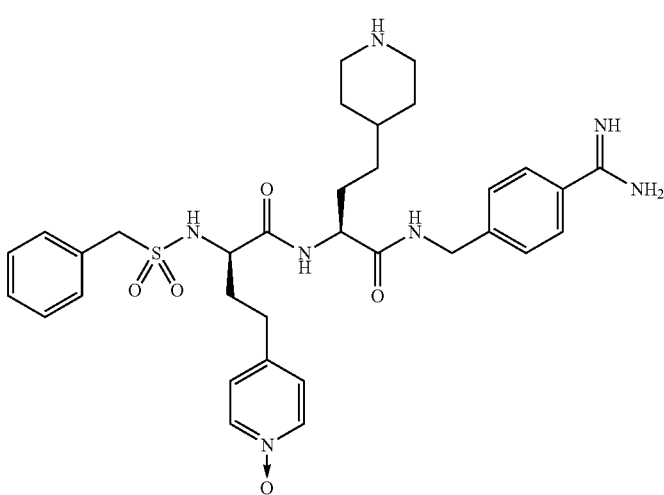 [SMILES: N=C(N)c1ccc(CNC(=O)[C@H](CCC2CCNCC2)NC(=O)[C@@H](CCc2cc[n+]([O-])cc2)NS(=O)(=O)Cc2ccccc2)cc1]

| h plasmin | Ki; nM | 5 |
| h PK | Ki; nM | 20 |
| h aPC | Ki; nM | 250 |
| h uKK | Ki; nM | >100,000 |
| h C1s | Ki; nM | 4,200 |
| h C1r | Ki; nM | >50,000 |
| h FIIa | Ki; nM | 9,000 |
| h FXa | Ki; nM | 120 |
| h FXIa | Ki; nM | 2,500 |
| h FXIIa | Ki; nM | n.d. |
| h t-PA | Ki; nM | n.d. |

TABLE 6-continued

| | | |
|---|---|---:|
| h plasmin | Ki; nM | 0.6 |
| h PK | Ki; nM | 1.5 |
| h aPC | Ki; nM | 1,700 |
| h uKK | Ki; nM | >200,00 |
| h C1s | Ki; nM | >25,000 |
| h C1r | Ki; nM | >30,000 |
| h FIIa | Ki; nM | 13,000 |
| h FXa | Ki; nM | 3,200 |
| h FXIa | Ki; nM | 920 |
| h FXIIa | Ki; nM | 1,300 |
| h t-PA | Ki; nM | 6,500 |

| | | |
|---|---|---:|
| h plasmin | Ki; nM | 1 |
| h PK | Ki; nM | 4 |
| h aPC | Ki; nM | 850 |
| h uKK | Ki; nM | >200,000 |
| h C1s | Ki; nM | 9,500 |
| h C1r | Ki; nM | >30,000 |
| h FIIa | Ki; nM | 4,900 |
| h FXa | Ki; nM | 400 |
| h FXIa | Ki; nM | 1,400 |
| h FXIIa | Ki; nM | 870 |
| h t-PA | Ki; nM | 2,400 |

| | | |
|---|---|---:|
| h plasmin | Ki; nM | 1 |
| h PK | Ki; nM | 1.5 |
| h aPC | Ki; nM | 800 |
| h uKK | Ki; nM | >100,000 |
| h C1s | Ki; nM | 6,500 |
| h C1r | Ki; nM | >100,000 |
| h FIIa | Ki; nM | 3,600 |
| h FXa | Ki; nM | 400 |
| h FXIa | Ki; nM | 600 |
| h FXIIa | Ki; nM | 400 |
| h t-PA | Ki; nM | n.d. |

ADDITIONAL REFERENCES

The following references provide background information, which may be useful in understanding the state of the art prior to the present invention:

Ashgar et al., *Biochim. Biophys. Acta* 438, 250-264, 1976
Collen et al., *J. Lab. Clin. Med.* 99, 76-83, 1982
Dixon, *Biochem. J.* 55, 170-171, 1953
Eriksson et al., *J. Thromb. Haemostasis* 1, 2490-2496, 2003
Fareed et al., *Ann. N. Y. Acad. Sci.* 370, 765-784, 1981
Francis et al., *New Engl. J. Med.* 349, 1703-1712, 2003
Garrett et al., *Bioorg. Med. Chem. Lett.* 9, 301-306, 1999

Garrett et al., *J. Pept. Res.* 52, 60-71, 1998
Griffin, *Proc. Natl. Acad. Sci. USA* 75, 1998-2002, 1978
Gustafsson et al., *Nature Reviews* 3, 649-659, 2004
Isobe, *Blood & Vessel* 12, 135-138, 1981
Kaplan, *Prog. Hemostasis Thromb.* 4, 127-175, 1978
Kettner et al., *J. Biol. Chem.* 265, 18289-18297, 1990
Kettner and Shaw, *Biochemistry* 17, 4778-4784, 1978
Künzel et al., *Bioorg. Med. Chem. Lett.,* 12, 645-648, 2002
Lawson et al., *Folia Haematol.* (Leipzig) 109, 52-60, 1982
Muramatu et al. *Hoppe-Seyler's Z. Physiol. Chem.* 363, 203-211, 1982
Muramatu and Fuji, *Biochim. Biophys. Acta* 242, 203-208, 1971
Muramatu and Fuji, *Biochim. Biophys. Acta* 268, 221-224, 1972
Ohno et al., *Thromb. Res.* 19, 579-588, 1980
Okada et al., *Bioorg. Med. Chem. Lett.* 10, 2217-2221, 2000
Okada et al., *Biopolymers* 51, 41-50, 1999
Ratnoff, *Blood* 57, 55-58, 1981
Robinson and Saiah, *Ann. Rep. Med. Chem.* 37, 85-94, 2002
Satoh et al., *Chem. Pharm. Bull.* 33, 647-654, 1985
Schechter and Berger, *Biochem. Biophys. Res. Comm.* 27, 157-162, 1967
Silverberg and Kaplan, *Blood* 60, 64-70, 1982
Stürzebecher et al., *Brazilian J. Med. Biol. Res.,* 27, 1929-1934, 1994
Stürzebecher et al., *J. Med. Chem.* 40, 3091-3099, 1997
Stürzebecher et al., *Zbl. Pharm. Pharmakother. Lab. Diagn.* 122, 240-241, 1983
Sucker H. et al., *Pharmazeutische Technologic,* 2nd circulation (1991), Georg Thieme Verlag, Stuttgart
Tada et al., *Biol. Pharm. Bull.* 24, 520-524, 2001
Teno et al. *Chem. Pharm. Bull.* 39, 2930-2936, 1991
*Thromb. Res.,* Suppl. VIII, 131-141, 1988
Tsuda et al., *Chem. Pharm. Bull.* 49, 1457-1463, 2001
Weitz, *Circulation,* 110, I-19-I-26, 2008
WO 1994/29336
WO 2000/041531
WO 2000/058346
WO 2001/096286
WO 2001/096366
WO 2002/062829
WO 2002/014349
WO 2003/076391
WO 2003/076457
DE 10212555
EP 1364960
U.S. Pat. No. 6,586,405
U.S. Pat. No. 5,786,328

It is understood that the examples and embodiments described herein are for illustrative purposes only and that various modifications or changes in light thereof will be suggested to persons skilled in the art and are to be included within the spirit and purview of this application and scope of the appended claims.

All documents, papers and published materials referenced herein, including books, journal articles, manuals, patent applications, published patent applications and patents, are expressly incorporated herein by reference in their entireties.

What is claimed is:

1. A method for therapeutic modulation of blood coagulation cascade or fibrinolysis, comprising administering to a patient in need thereof an effective amount of one or more compounds having the following formula:

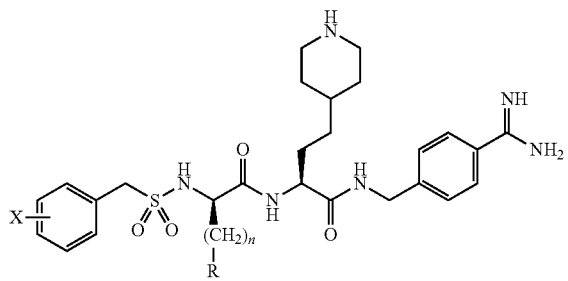

or a pharmaceutically acceptable salt thereof; wherein X is selected from the group consisting of H, $CO_2H$, and $CO_2R'$; n ranges from 0 to 3; and R is selected from the group consisting of phenyl, pyridyl, tetrazolyl, and piperidinyl; wherein R is unsubstituted or substituted by one or more substituents selected from the group consisting of halogen, R', OR', SR', S=(O)R', S(=O)$_2$R', S(=O)$_2$NHR', S(=O)2NR'$_2$, CN, NH$_2$, NHR', NR'$_2$, NHS(=O)$_2$R', NHC(=O)R', NHC(=O)OR', NHC(=O)NHR', NHC(=O)NR'$_2$, C(=O)R', C(=O)CH$_2$OR', CO$_2$R', C(=O)NHR', and C(=O)NR'$_2$; wherein when R is pyridyl it is optionally a pyridine N-oxide; and wherein each R' is independently $CF_3$ or $C_1$ to $C_4$ lower alkyl or cycloalkyl.

2. The method according to claim 1, wherein n is 2 or 3.

3. The method according to claim 1, wherein R is selected from the group consisting of phenyl, 4-pyridyl, 4-pyridyl N-oxide and 4-piperidinyl.

4. The method according to claim 3, wherein R is selected from the group consisting of unsubstituted phenyl, unsubstituted 4-pyridyl, unsubstituted 4-pyridyl N-oxide and unsubstituted 4-piperidinyl.

5. The method according to claim 1, wherein n is 0 and R is phenyl.

6. The method according to claim 1, wherein n is 2 or 3 and R is 4-piperidinyl; wherein the nitrogen of said piperidinyl bears a substituent selected from the group consisting of C(=O)R', C(=O)CH$_2$OR', CO$_2$R', C(=O)NHR', and C(=O)NR'$_2$.

7. The method according to claim 1, wherein a pharmaceutical composition is administered to the patient, wherein the pharmaceutical composition comprises one or more of the compounds of claim 1, and one or more pharmaceutically acceptable carriers or excipients.

* * * * *